(12) United States Patent
Chow et al.

(10) Patent No.: US 7,601,331 B2
(45) Date of Patent: Oct. 13, 2009

(54) NIR-SENSITIVE NANOPARTICLE

(75) Inventors: Gan Moog Chow, Singapore (SG); Mei Chee Tan, Singapore (SG); Lei Ren, Xiamen (CN); Jackie Yi-Ru Ying, Singapore (SG)

(73) Assignee: National University of Singapore, Singapore (SG)

( * ) Notice: Subject to any disclaimer, the term of this patent is extended or adjusted under 35 U.S.C. 154(b) by 895 days.

(21) Appl. No.: 10/985,018

(22) Filed: Nov. 10, 2004

(65) Prior Publication Data

US 2006/0099146 A1    May 11, 2006

(51) Int. Cl.
*A61K 51/00* (2006.01)
*A61M 36/14* (2006.01)

(52) U.S. Cl. .................... 424/1.29; 424/1.37; 424/1.65; 424/9.1; 424/9.6; 424/417

(58) Field of Classification Search ................ 424/1.11, 424/1.29, 1.37, 1.65, 1.69, 1.81, 9.1, 9.3, 424/9.4, 9.5, 9.6, 400, 408, 417, 450, 451, 424/456, 463, 464, 484; 206/223, 569, 570
See application file for complete search history.

(56) References Cited

OTHER PUBLICATIONS

Matthews van Holde, Biochemistry, 1990, pp. 133-155.*
Allen, T.M., et al., "Ligand-Targeted Therapeutics in Anticancer Therapy," *Nature Reviews Cancer*, Oct. 2002, pp. 750-763, vol. 2. Nature Publishing Group.
Averitt, R.D. et al., "Plasmon Resonance Shifts of Au-coated $Au_2S$ Nanoshells: Insight into Multicomponent Nanoparticle Growth," *Physical Review Letters*, Jun. 2, 1997, pp. 4217-4220, vol. 78., No. 22. The American Physical Society.

Dolmans, D.E.J.G.J. et al., "TIMELINE: Photodynamic therapy for cancer," *Nature Reviews Cancer*, May 2003, pp. 380-387, vol. 3. Nature Publishing Group.
Frangioni, J.V., "In vivo near-infrared fluorescence imaging," *Current Opinion in Chemical Biology*, 2003, pp. 626-634, vol. 7.
Hirsch, L.R. et al., "A Whole Blood Immunoassay Using Gold Nanoshells," *Analytical Chemistry*, May 15, 2003, pp. 2377-2381, vol. 75. American Chemical Society.
Hirsch, L.R. et al., "Nanoshell-mediated near-infrared thermal therapy of tumors under magnetic resonance guidance," *Proc. Natl. Acad. Sci USA*, Nov. 11, 2003, pp. 13549-13554, vol. 100, No. 23.

(Continued)

*Primary Examiner*—D L Jones
(74) *Attorney, Agent, or Firm*—Rothwell, Figg, Ernst & Manbeck

(57) ABSTRACT

It is provided a Near Infrared Sensitive (NIR-sensitive) nanoparticle complex comprising a NIR-sensitive nanoparticle and surfactant(s) adsorbed on the nanoparticle, wherein the surfactant is at least one surfactant selected from:

(a) $HS-(C_XH_Y)_n-(C_ZH_W)_m-R^5$ with $R^1, R^2$ on the first carbon group and $R^3, R^4$ on the second carbon group wherein X=1-9; Y=0-9; n=0-9; Z=1-9; W=0-9; m=0-9; each of $R^1, R^2, R^3$ and $R^4$, if present, is H, substituted or unsubstituted $C_1-C_6$ alkyl, substituted or unsubstituted $C_1-C_6$ aryl, HS, COOH, $NH_2$ or OH; $R^5$ is COOH, $NH_2$ or OH; with the proviso that n+m is <10;
(b) an amino acid having the structure in (a), wherein X=1; Y=2; Z=1; W=1; $R^1, R^2$ and $R^4$ are not present; $R^3$ is $NH_2$; and $R^5$ is COOH; or (c) a peptide, wherein the peptide comprise at least one amino acid (b). Further, it is provided a NIR-sensitive nanoparticle complex(es) having biomolecule(s), for example drug(s), loaded on the surfactant(s).

21 Claims, 18 Drawing Sheets

OTHER PUBLICATIONS

Ishikawa, K. et al., "Structure and electrical properties of $Au_2S$," *Solid State Ionics*, 1995, pp. 60-66. vol. 79. Elsevier Science B.V.

Kamat, P.V., "Photophysical, Photochemical and Photocatalytic Aspects of Metal Nanoparticles," *J. Phys. Chem. B*, 2002, pp. 7729-7744, vol. 106. American Chemical Society.

Oldenburg, S.J. et al., "Nanoengineering of optical resonances," *Chemical Physics Letter*, May 22, 1998, pp. 243-247, vol. 288. Elsevier Science B.V.

Panyam, J. et al., "Biodegradable nanoparticles for drug and gene delivery to cells and tissue," *Advanced Drug Delivery Reviews*, 2003, pp. 329-347, vol. 55. Elsevier Science B.V.

Ren, L. et al., "Synthesis of nir-sensitive $Au$-$Au_2S$ nanocolloids for drug delivery," *Materials Science and Engineering C*, 2003, pp. 113-116, vol. 23. Elsevier Science B.V.

Sato, S., et al., "Nanosecond, High-Intensity Pulsed Laser Ablation of Myocardium Tissue at the Ultraviolet, Visible, and Near-Infrared Wavelengths: In-Vitro Study," *Lasers in Surgery and Medicine*, 2001, pp. 464-473, vol. 29. Wiley-Liss, Inc.

Sershen, S. et al., "Implantable, polymeric systems for modulated drug delivery," *Advanced Drug Delivery Reviews*, 2002, pp. 1225-1235, vol. 54. Elsevier Science B.V.

Weissleder, R., "A clearer vision for in vivo imaging," *Nature Biotechnology*, Apr. 2001, pp. 316-317, vol. 19. Nature Publishing Group.

Zhou, H.S. et al.,, "Controlled synthesis and quantum -size effect in gold-coated nanoparticles," *Physical Review. B*, Oct. 15, 1994, pp. 12052-12057, vol. 50. the American Physical Society.

* cited by examiner

NIR-SENSITIVE NANOPARTICLE

FIELD OF THE INVENTION

The present invention relates to NIR-sensitive nanoparticle complex comprising NIR-sensitive nanoparticle and one or more selected surfactants for biomolecule delivery. In particular for drug delivery.

BACKGROUND OF THE INVENTION

With more than 10 million people diagnosed with cancer each year and 12% of the deaths worldwide believed to be caused by cancer, there has been an increasing motivation for alternative therapies (who.int/cancer/en). The invasive nature of surgery and adverse effects of conventional chemotherapy and radiotherapy have limited the success of cancer treatment. Frequent administrations of toxic chemotherapy and radiotherapy agents are necessary to minimise their systemic concentration. A more efficient strategy is the delivery of these toxic agents to the tumour sites using targeted delivery systems.

Liposomes and polymeric drug carriers less than 100 nm had been reported to have a tendency to be localised at tumours (Panyam and Labhasetwar, 2003; Allen T M, 2002). This had been attributed to the increased permeability through the tumour vasculature where the cell gap junctions are between 100 to 600 nm. Besides the localisation at tumours and increased surface-to-volume ratio, nanoparticles exhibited other attractive properties unique to its size.

Near infrared (NIR) sensitive nanoshells (Oldenburg et al., 1998) with size and shell thickness dependent properties, are being investigated for applications in hyperthermia (Hirsch et al., Proc Natl Acad Sci USA, 2003), temperature-responsive delivery systems (Sershen and West, 2002) and immunoassays (Hirsch et al.; 2003, Anal Chem). NIR light ($\lambda$=650-1000 nm) with its superior propagation in living tissues and signal to background ratio, had been exploited for biomedical imaging (Frangioni J V, 2003), photoablation (Sato et al., 2001) and photodynamic therapy (Dolmans et al., 2003). Haemoglobin and melanin are the major NIR absorbers, while the composition, size and morphology of tissue components also affect the optical penetration. NIR light had been reported to travel through 10 cm of breast tissue and 4 cm of skull tissue using microwatt sources (Weissleder, 2001).

A drug-delivery system, comprising NIR sensitive Au—$Au_2S$ nanoparticles with 11-mercaptoundecanoic acid (MUA) adsorbed onto the surface of the nanoparticles and subsequently loaded with cisplatin, was suggested by Ren and Chow, 2003. It was suggested that when NIR light is applied, the cisplatin is released from the nanoparticles to destroy cancerous cells. It has been suggested that such a drug delivery system has the potential to be more efficient, to have reduced toxicity and improved patient compliance and convenience compared to conventional cancer treatments.

Although the system described above has been suggested as a potential drug delivery system, there is a need in the art for a further investigation for a better understanding of the mechanism of interaction between NIR light and NIR sensitive Au—$Au_2S$ nanoparticles as well as for the finding of an efficient system for the delivery of drug to a tumour site.

SUMMARY OF THE INVENTION

The present invention addresses the problems above, and provides an improved NIR-sensitive nanoparticle complex for biomolecules delivery.

According to one aspect, the invention provides a NIR-sensitive nanoparticle complex comprising a NIR-sensitive nanoparticle and surfactant(s) adsorbed on the nanoparticle, wherein the surfactant is at least one surfactant selected from:

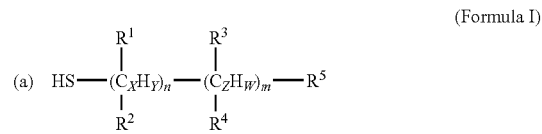

(Formula I)

wherein X=1-9; Y=0-9; n=0-9; Z=1-9; W=0-9; m=0-9;

each of $R^1$, $R^2$, $R^3$ and $R^4$ independently, if present, is H, substituted or unsubstituted $C_1$-$C_6$ alkyl, substituted or unsubstituted $C_1$-$C_6$ aryl, HS, COOH, $NH_2$ or OH;

$R^5$ is COOH, $NH_2$ or OH;

with the proviso that n+m is <10;

(b) an amino acid having the structure in (a), wherein X=1; Y=2; Z=1; W=1; $R^1$, $R^2$ and $R^4$ are not present; $R^3$ is $NH_2$; and $R^5$ is COOH; or (c) a peptide, wherein the peptide comprise at least one amino acid (b).

Accordingly, mercaptoundecanoic [$HS(CH_2)_{10}COOH$; also herein indicated as MUA] is not within the scope of the present invention.

In particular, the surfactant(s) of the invention may be at least one or a mixture of the following:

(i) a surfactant, comprising thiol and carboxylic acid functional groups, selected from mercaptosuccinic acid, mercaptobenzoic acid, penicillamine, mercaptopropioinyl glycine, thioldiacetic acid, thiodipropionic acid, and cysteine hydrochloride (ii) a surfactant, comprising thiol and amine functional groups, selected from cysteine, mercaptoethylamine, thioguanine, and thioacetamide;

(iii) a surfactant, comprising thiol and hydroxyl groups, selected from mercaptoethanol, thiodiethanol, thioglucose, thioglycerol and cysteine-OH;

(iv) cysteine; and/or (v) a peptide comprising cysteine.

The (v) cysteine-containing peptide may be a peptide having the sequence of SEQ ID NO:1.

More in particular, in the surfactant(s) of Formula (I) n+m is 1-4, preferably 1 or 2. More preferably, the surfactant(s) of the invention is: $HSCH_2COOH$ and/or $HS(CH_2)_2COOH$.

According to another aspect, the invention provides a NIR-sensitive nanoparticle(s) further comprising at least one biomolecule loaded on the surfactact(s).

The biomolecule is preferably a drug. More preferably, but not limited to, an anti-cancer drug. In particular, the drug is selected from the group consisting of alkylating agents, antimetabolites, plant alkaloids, anti-tumour antibiotics, monoclonal or polyclonal antibody, a cytokine, an antisense oligonucleotide, siRNA, and a gene-targeting vector. For example, the drug may be cisplatin, carboplatin, nedaplatin, satraplatin, methotraxate and/or doxorubicin.

According to a particular aspect, the invention provides a NIR-sensitive nanoparticle complex comprising a NIR-sensitive nanoparticle coated with at least a surfactant, and at least one drug loaded on the surfactant(s), wherein the surfactant is $HSCH_2COOH$ and/or $HS(CH_2)_2COOH$, and the drug is cisplatin, carboplatin, nedaplatin, satraplatin, methotraxate and/or doxorubicin.

The nanoparticle has a diameter of preferably between 20 nm to 500 nm. Preferred range of unmodified NIR-sensitive nanoparticles is ~30 to 50 nm.

The nanoparticle may be a nanocomposite of gold and sulphur. In particular, the nanoparticle is a nanocomposite of crystalline Au and amorphous $Au_X$—$S_Y$, $(Au_z)_{crystalline}$ $(Au_x$—$S_y)_{amorphous}$, wherein $3 \leq (z+x) \leq 30$ for $y=1$. More in particular, the nanoparticle is Au—$Au_2S$ nanoparticle. According to another aspect, the present invention provides a method of preparing the NIR-sensitive nanoparticle complex according to any embodiment of the invention, comprising:

providing NIR-sensitive nanoparticle; and coating the nanoparticle with at least one surfactant of the invention to form a nanoparticle complex.

The method further comprises loading a biomolecule, for example a drug, on the surfactant(s).

According to another aspect, the invention provides a drug delivery system, comprising:

a source of NIR;

means for delivery of NIR to a tumour;

at least one drug loaded on NIR-sensitive nanoparticles complex, according to any embodiment of the invention, absorbing the NIR; and means for administration of the drug loaded NIR-sensitive nanoparticle complex.

The source of NIR may be a laser source. For example, the laser source is Nd:YAG. The means for delivery of NIR may comprise optical fibres or endoscopes.

Preferably, each nanoparticle has a diameter of between 20 nm to 500 nm.

According to another aspect, the invention provides a method of treating a tumour, comprising the steps of:

providing NIR-sensitive nanoparticles complex according to any embodiment of the invention, and loading a drug on the surfactant(s);

introducing the drug loaded NIR-sensitive nanoparticle complex to or in the proximity of a tumour; and irradiating the tumour or the tumour area with NIR;

The drug may be selected from the group consisting of alkylating agents, anti-metabolites, plant alkaloids, anti-tumour antibiotics, monoclonal or polyclonal antibody, a cytokine, an antisense olignucleotide, siRNA, and a gene-targeting vector. In particular, the drug is cisplatin, carboplatin, nedaplatin, satraplatin, methotraxate and/or doxorubicin.

The tumour may be an organ selected from the group consisting of breast, lung, brain, liver, bone, skin, kidney, GI (gastrointestinal (GI) tract) organ, prostrate, bone, bladder and gynaecological organ. The drug loaded NIR-sensitive nanoparticle complex may be administered by any means known in the art, for example by oral, intramuscular, subcutaneous, intravenous or intrathecal administration.

According to another aspect, the present invention provides a kit comprising:

NIR-sensitive nanoparticle(s) according to any embodiment of the invention; and one or more surfactant(s) according to any embodiment of the invention.

The kit may further comprise a biomolecule, in particular a drug as specified above.

According to another aspect, the invention provides a method of modulating biomolecule loading and/or releasing efficiency on/from a NIR-sensitive nanoparticle complex, or of modulating the optical properties of a NIR-sensitive nanoparticle complex, the complex comprising surfactant(s) adsorbed on NIR-sensitive nanoparticle, comprising varying the chain length of surfactant(s) adsorbed on the NIR-sensitive nanoparticle.

According to another aspect, the present invention provides a method for colorimetric sensor detection of biomolecule(s), for example, toxin(s) and/or toxic gas(es) comprising varying the optical properties of a nanoparticle complex according to any embodiment of the invention. The change (or variation) of the optical properties may be carried out by varying the chain length of the surfactant(s) as described above.

Further, the present invention provides a method of modulating binding affinity and/or binding recognition of the nanoparticle complex ligand(s) (sensors) with the respective receptor(s). The modulation of the binding affinity and/or binding recognition of particular kind of biomolecule(s), that is, ligand(s) (sensors) loaded on the nanoparticle complex according to any embodiment of the invention can be carried out, for example, by altering the surfactant(s) interaction(s). This can be carried out, for example, by varying the chain length of the surfactant(s).

DETAILED DESCRIPTION OF THE INVENTION

Figure 1:
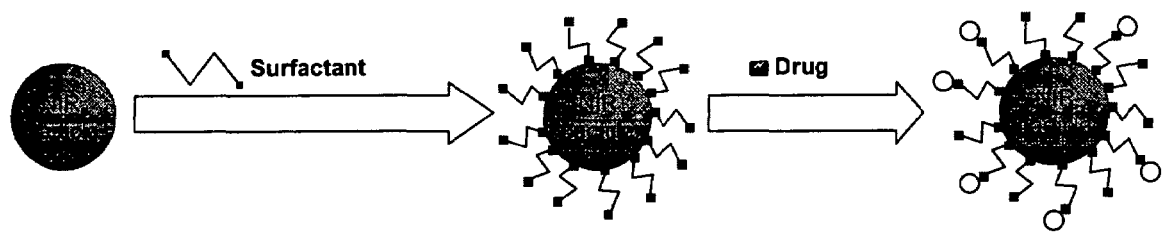
FIG. 1 is a schematic illustration of NIR targeted drug delivery system.

As noted above, near-infrared (NIR) radiation is non-destructive to human tissues. It may therefore be useful for exploiting this property of NIR. The present invention incorporates the outstanding properties of tissue penetrative NIR light and NIR-sensitive nanoparticles to develop minimally invasive delivery system that triggers drug release at tumours. This can potentially reduce the deleterious effects of anti-cancer drugs and allow the treatment of surgically inoperable tumours.

Accordingly, one aspect of the present invention provides a near-infrared sensitive nanoparticle complex comprising a NIR-sensitive nanoparticle and surfactant(s) adsorbed on the nanoparticle, wherein the surfactant is at least one surfactant selected from:

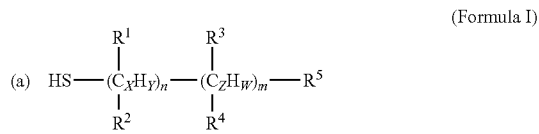

(Formula I)

wherein X=1-9; Y=0-9; n=0-9; Z=1-9; W=0-9; m=0-9;

each of $R^1$, $R^2$, $R^3$ and $R^4$ independently, if present, is H, substituted or unsubstituted $C_1$-$C_6$ alkyl, substituted or unsubstituted $C_1$-$C_6$ aryl, HS, COOH, $NH_2$ or OH;

$R^5$ is COOH, $NH_2$ or OH;

with the proviso that n+m is <10;

(b) an amino acid having the structure in (a), wherein X=1; Y=2; Z=1; W=1; $R^1$, $R^2$ and $R^4$ are not present; $R^3$ is $NH_2$; and $R^5$ is COOH; or (c) a peptide, wherein the peptide comprise at least one amino acid (b).

Accordingly, mercaptoundecanoic acid $(HS(CH_2)_{10}COOH$, herein also indicated as MUA) is not within the scope of the present invention.

"Nanoparticles" as used herein, is defined as a particle having a diameter of from 1 to 1000 nanometers (nm), having any size, shape or morphology. In particular, the nanoparticle has a diameter between 20 and 500 nm. Preferred range of unmodified NIR-sensitive nanoparticles is ~30 to 50 nm. As used herein, "nanoshell" is a nanoparticle having a discrete dielectric or semiconducting core section surrounded by one or more conducting shell layers. A "nanoshell" is a subspecies of nanoparticles characterised by the discrete core/shell structure. Nanoparticle means one or more nanoparticles and nanoshell means one or more nanoshells. Further, shell means one or more shells.

The term "surfactant", as used herein, refers to a surface active agent that lowers the surface tension. It contains both hydrophilic and hydrophobic components and is semi-soluble in both organic and aqueous solvents. For example, surfactants tend to clump up when in solution, forming a surface between fluid and air with hydrophobic tails in the air and the hydrophilic heads in the fluid.

For the purposes of this invention, the term "nanoparticle complex" refers to a nanoparticle which has a surfactant adsorbed onto its surface, while a near-infrared sensitive (NIR) nanoparticle refers to a nanoparticle that is activated when it is irradiated with near-infrared light. Near-infrared light has a wavelength from 650 to 1000 nm.

As used herein, the term "alkyl" refers to a straight or branched, monovalent, saturated aliphatic chain of preferably 1 to 6 carbon atoms, including normal, iso, neo and tertiary. "Alkyl" includes, but is not limited to, methyl, ethyl, propyl, isopropyl, butyl, iso-butyl, sec butyl, tert butyl, amyl, isoamyl, neoamyl, hexyl, isohexyl, neohexyl, and the like; cycloalkyl group such as cyclopropyl, cyclobutyl, cyclopentyl, cyclohexyl and the like, the cycloalkyl group may be substituted. The alkyl may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may contain one or more O, S, S(O), or $S(O)_2$ atoms.

The term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, biphenyl, naphthyl, furanyl, pyrrolyl, thiophenyl, pyridinyl, indolyl, benzofuranyl, benzothiophenyl, quinolinyl, isoquinolinyl, imidazolyl, thiazolyl, pyrazinyl, pyrimidinyl, purinyl and pteridinyl and the like.

The term "lower" refers to a group having between one to six carbon atoms.

Accordingly, any suitable surfactant within the definition of Formula (I) may be used for the purposes of the present invention. Suitable surfactants are for example described in the Sigma Aldrich catalogue, 2004-2005. In particular, the surfactant used may be at least one or a mixture of the following:

(i) a surfactant, comprising thiol and carboxylic acid functional groups, selected from mercaptosuccinic acid, mercaptobenzoic acid, penicillamine, mercaptopropioinyl glycine, thioldiacetic acid, thiodipropionic acid, and cysteine hydrochloride;

(ii) a surfactant, comprising thiol and amine functional groups, selected from cysteine, mercaptoethylamine, thioguanine, and thioacetamide;

(iii) a surfactant, comprising thiol and hydroxyl groups, selected from mercaptoethanol, thiodiethanol, thioglucose, thioglycerol and cysteine-OH;

(iv) cysteine; and/or (v) a peptide comprising cysteine.

For example, in the surfactant(s) of Formula (I), n+m is 1-9, 1-8, 1-7, 1-6, 1-5, 1-4, 1-3, 1-2, or 1. In particular, n+m is 1-4, preferably 1 or 2, and each one of $R^1$, $R^2$, $R^3$, and $R^4$, independently, is not present or is H. More in particular, surfactant(s) of the invention may be $HSCH_2COOH$ and/or $HS(CH_2)_2COOH$. The cysteine-containing peptide of (v) may be a peptide of SEQ ID NO:1.

Suitable surfactants within the definition of Formula (I) would include those with the thiol and carboxylic acid functional groups (e.g. mercaptosuccinic acid, mercaptobenzoic acid, penicillamine, mercaptopropioinyl glycine, thioldiacetic acid, thiodipropionic acid, cysteine hydrochloride), the thiol and amine functional groups (e.g. cysteine, mercaptoethylamine, thioguanine, thioacetamide), the thiol and hydroxyl groups (e.g. mercaptoethanol, thiodiethanol, thioglucose, thioglycerol, cysteine-OH) and cysteine and peptides comprising cysteine (e.g. laminin fragment 925-933: CYS-ASP-PRO-GLY-TYR-ILE-GLY-SER-ARG (SEQ ID NO:1)). Other suitable surfactants are described in the Sigma Aldrich catalogue, 2004-2005 (herein incorporated by reference). The molecules with free amine, hydroxyl or carboxyl groups could be attached to these surfactants include anti-cancer drugs (e.g. carboplatin, nedaplatin, JM216, methotrexate and doxorubicin) as well as proteins and glycoproteins (e.g. Herceptin).

According to a further aspect, the nanoparticle may be any suitable nanoparticle known in the art, for example, a metallic, semiconductor, carbon, graphite or polymer nanoparticle. Nanoparticles, in particular nanocomposites, of any morphology, according to any of the following combinations i.e. metal and semiconductor, metal and organic compound, semiconductor and organic compound, that exhibit a characteristic optical absorption within the NIR region 650-1000 nm, are also within the scope of the present invention. In particular, the nanoparticle is a nanocomposite of gold and sulphur. Even more in particular, the nanoparticle is $Au$—$Au_2S$. Further, the nanoparticle may be a nanocomposite of crystalline Au and amorphous $Au_X$—$S_Y$. In particular, $(Au_z)_{crystalline}$ $(Au_x$—$S_y)_{amorphous}$, wherein $3 \leq (z+x) \leq 30$ for $y=1$.

According to another aspect, the NIR-sensitive nanoparticle complex further comprises a biomolecule loaded on the surfactant. The biomolecule may be a drug, in particular, an anti-cancer drug. The biomolecule may be a drug selected from the group consisting of alkylating agents, anti-metabolites, plant alkaloids, anti-tumour antibiotics, monoclonal or polyclonal antibody, a cytokine, an antisense olignucleotide, siRNA, and a gene-targeting vector. When the drug is loaded onto the surfactant, the NIR-sensitive nanoparticle is referred to as a drug loaded NIR-sensitive nanoparticle complex. Further, suitable drugs are described in the Sigma Aldrich catalogue (herein incorporated by reference).

For example, alkylating agents act directly on DNA, causing cross-linking of DNA strands, abnormal base pairing, or DNA strand breaks, thus preventing a cell from dividing. This is particularly advantageous in the treatment of cancer. Alkylating agents kill the cell in various and multiple phases of the cell cycle. Although alkylating cells may be used for most types of cancer, they are generally of greatest value in treating slow-growing cancers. Examples of alkylating agents include chlorambucil, cyclophosphamide, thioepa and busulfan.

Anti-metabolites replace natural substances as building blocks in DNA molecules, thereby altering the function of enzymes required for cell metabolism and protein synthesis. In other words, they mimic nutrients that the cell needs to grow, tricking the cell into consuming them, so it eventually starves to death. Anti-metabolites are most effective during the S-phase of cell division. Examples of anti-metabolites include purine antagonists, pyrimidine antagonists and folate antagonists.

Plant alkaloids are anti-tumour agents derived from plants. They act specifically by blocking the ability of a cancer cell to divide and become two cells. Examples of plant alkaloids include actinomycin D, doxorubicin and mitomycin.

Anti-tumour antibiotics are cell cycle non-specific. They act by binding with DNA and preventing RNA synthesis, a key step in the creation of proteins, which are necessary for cell survival. These types of drugs cause the strands of genetic material that make up DNA to uncoil, thereby preventing the cell from reproducing. Doxorubicin, mitoxantrone and bleomycin are some example of anti-tumour drugs.

According to a particular aspect, the drug may be any one or a combination of cisplatin, carboplatin, nedaplatin, satraplatin, methotraxate or doxorubicin.

Another aspect of the present invention is a NIR-sensitive nanoparticle complex as described above, wherein the surfactant may be either $HSCH_2COOH$ or $HS(CH_2)_2COOH$, or a combination thereof, and the biomolecule loaded onto the surfactant is a drug comprising one or a combination of cisplatin, carboplatin, nedaplatin, satraplatin, methotraxate and/or doxorubicin.

Another aspect of the present invention is a method of preparing the NIR-sensitive nanoparticle complex described above. The method comprises the steps of:
  providing the NIR-sensitive nanoparticle; and
  coating the nanoparticle with at least one surfactant according to any embodiment of the invention to form the nanoparticle complex.

The method may further comprise a step of loading a biomolecule to the surfactant(s), wherein the biomolecule may be any suitable drug. For example, the drug may be any one of the drugs already described.

The drug loaded NIR-sensitive nanoparticle complex according to the present invention may be especially useful in drug delivery. In particular, the NIR-sensitive nanoparticle complex may be used as a vehicle and/or carrier of drugs in drug delivery. Accordingly, another aspect of the present invention provides a drug delivery system comprising:
  a source of NIR;
  means for delivery of NIR to a tumour;
  at least one drug loaded on NIR-sensitive nanoparticle complexes absorbing the NIR; and
  means for administration of the drug loaded NIR-sensitive nanoparticle complex, wherein the surfactant adsorbed on the nanoparticle to form the NIR-sensitive nanoparticle complex is any surfactant as already described.

The at least one drug loaded to the NIR-sensitive nanoparticle complex may be any drug or a combination or drugs as already described.

An example of such a drug delivery system is as shown in FIG. 1.

Any suitable source of NIR may be used for the purposes of the present invention. The purpose of the NIR is to irradiate the drug loaded NIR-sensitive nanoparticle to trigger the release of the drug near or within the tumour. The advantage of using NIR is that it maximises the penetration of light and minimises damage to surrounding tissue. It is not appreciably absorbed by tissues. For example, the source of NIR may be a laser source. In particular, the NIR source is a laser source Nd:YAG (Neodymium-doped Yttrium Aluminium Garnet). A Nd:YAG laser at 1064 nm may be used to trigger drug release. The drug release may be attributed to the photophysical and photothermal effects induced by NIR irradiation. With reference to photoeffects of nanoparticles, a useful reference in Kamat, J. of Phys. Chem. B, 106 (32), 2002, 7729.

Nd:YAG laser is one of the most versatile laser sources. The relative robustness and compactness of the laser and the possibility for the 1.06 micron light it produces to be transmitted to the required area via silica optical fibres, are two features which contribute to its success. Typically, it has a frequency between 5 and 50 Hz. The Nd:YAG crystals in the laser can be pumped either using white light flashlamps or, more efficiently, using laser diodes. The latter methods are used to produce high quality beams, which can be focussed on smaller spots (and therefore produce higher power densities) than the flashlamp pumped lasers.

The means for delivery of NIR may comprise optical fibres and endoscopes. The optical fibres may be inserted in a needle. The laser may also be delivered through the skin surface. However, any suitable means for delivery of NIR known to a skilled person may be used.

The drug delivery system may further comprise an electronic system or means for monitoring the NIR light being supplied.

The NIR-sensitive nanoparticle complex of the present invention may also be used for the delivery of other therapeutic agents such as growth factors, for local hyperthermia and even used in biosensors.

Yet another aspect of the present invention is a method of treating tumour, comprising the steps of:
  providing (synthesising) NIR-sensitive nanoparticle complexes, the nanoparticle complex comprising NIR-sensitive nanoparticles coated with surfactant(s) and a drug loaded on the surfactant(s);
  introducing the drug loaded NIR-sensitive nanoparticle complex to or in the proximity of a tumour; and
  irradiating the tumour or the tumour area with NIR;

wherein the surfactant and drug is as described above.

The method may further comprise the step of monitoring the amount of NIR light the tumour has been irradiated with.

According to a further aspect, the tumour is in an organ selected from the group consisting of breast, lung, brain, liver, bone, skin, kidney, GI organ, prostrate, bladder and gynaecological organ. However, the tumour may be located in any other organ to which the present invention may relate to. In particular, the present invention relates to the treatment of the cancer of bone, wherein the bone comprises a surgically inoperable tumour. One of the current available solutions for treating such bone cancer is amputation. Another solution that is currently available is chemotherapy, but the success rate is low.

Further, the drug loaded NIR-sensitive nanoparticle complex may be administered by any suitable means known in the art. For example, it may be administered by means of oral, intramuscular, subcutaneous, intravenous or intrathecal administration.

According to another aspect, the invention relates to a method of varying the length of the surfactant(s) so as to modulate the efficiency of loading of the biomolecule(s) on the surfactant(s) as well as to modulate the NIR optical properties of the NIR-sensitive nanoparticle complex(es). In particular, the modulation is obtained by varying the chain length of surfactants (control) and determining the improved efficiency of loading biomolecule(s) on the modified surfactant(s), and/or improved efficiency of releasing biomolecule(s) from the modified surfactant(s) following NIR (light) irradiation.

The surface-modification of NIR-sensitive nanoparticles with surfactants faciliates the binding of functional molecules, such as biomolecules. Suitable surfactants exhibit compatible NIR optical properties with the NIR-sensitive nanoparticles, and have functional groups reactive to both the nanoparticle and desired molecules. The inorganic-organic surface interactions between the surfactants and nanoparticles may be used to modulate (manipulate) the optical properties of this biomolecule delivery system (for example drug delivery system). For the same number of functional groups on each surfactant, the reactivity and number of binding sites may be modified by altering the surfactant intermolecular and surfactant-particle interactions through differences in the surfactant chain length. The alteration of surfactant interactions to control the binding intensity would be applicable to systems surface functionalised with biomolecules, for example drugs or targeting ligands. The efficiency of this system was demonstrated using mercaptoacetic acid (MAA) and mercaptopropionic acid (MPA) compared to the use of mercaptoundecanoic acid (MUA), where the optical properties of the NIR-sensitive nanoparticles were altered using these organic surfactants, as seen in the Examples below. In addition, the different binding intensities of an anti-cancer drug, such as cisplatin, using the above-mentioned molecular linkers with different chain lengths was demonstrated.

Accordingly, the present invention provides a method of modulating the biomolecule loading efficiency on a NIR-sensitive nanoparticle complex, according to any embodiment of the invention, comprising varying the chain length of surfactant(s) adsorbed on the NIR-sensitive nanoparticle(s).

Preferably, the surfactant(s) is at least one surfactant or a mixture thereof of the surfactant of Formula (I).

In particular, the method is a method for increasing the biomolecule loading efficiency comprising varying the chain length of the surfactant(s) of Formula (I), so that the biomolecule loading efficiency is higher (increased) than the efficiency of biomolecules loaded on nanoparticle complex having a control (reference) surfactant. The control surfactant may be MUA or any other surfactant(s) whose biomolecule loading efficiency is desired to be improved (increased).

According to another aspect, the invention provides a method for modulating the optical properties of a NIR-sensitive nanoparticle complex, according to any embodiment of the invention, comprising varying the chain length of surfactant(s) adsorbed on the NIR-sensitive nanoparticle(s). Altering the optical properties of NIR-sensitive nanoparticle complex and NIR-sensitive nanoparticle complex having biomolecule loaded on them enable a change in the sensitivity of the biomolecule loaded NIR-sensitive nanoparticle complex. For example, a change in sensitivity of the optical trigger of biomolecule release of the biomolecule delivery system.

Accordingly, the invention also provides a method for modulating the release of biomolecule(s), for example drug(s), from biomolecule loaded NIR-sensitive nanoparticle complex(es) by altering the optical properties of the nanoparticle complex by varying the chain length of surfactant(s).

Preferably, the surfactant(s) is at least one surfactant or a mixture thereof of the surfactant of Formula (I).

In particular, the method is a method for modulating the optical properties by increasing the biomolecule releasing efficiency comprising varying the chain length of the surfactant(s) of Formula (I), so that the biomolecule releasing efficiency is higher (increased) than the efficiency of biomolecules loaded on nanoparticle complex having a control (reference) surfactant. The control surfactant may be MUA or any other surfactant(s) whose biomolecule releasing efficiency is desired to be improved (increased).

Considering the change in optical properties (and photophysical properties) upon exposure to NIR light, the surface-modified (with biomolecules, for example, with antibodies and other organic ligands) NIR-sensitive nanoparticles and/or nanoparticle complex(es) may be used as colorimetric sensors for biomolecules, for example toxins and/or toxic gas(es), as well as in molecular assays. Accordingly, the present invention also provides a method for colorimetric sensor detections of biomolecule(s), for example, toxin(s) and/or toxic gas(es) comprising varying the optical properties of a nanoparticle complex according to any embodiment of the invention. The change (or variation) of the optical properties may be carried out by varying the chain length of the surfactant(s) as described above.

Further, the present invention provides a method of modulating binding affinity and/or binding recognition of the nanoparticle complex ligand(s) (sensors) with the respective receptor(s). The modulation of the binding affinity and/or binding recognition of particular kind of biomolecule(s), that is, ligand(s) (sensors) loaded on the nanoparticle complex according to any embodiment of the invention can be carried out, for example, by altering the surfactant(s) interaction(s). This can be carried out, for example, by varying the chain length of the surfactant(s). Examples of binding between some ligands and receptors is provided in Table 1 below.

TABLE 1

Table showing examples of some ligands binding with receptors.
(Source: Allen TM, 2002)

| Recognition ligand/sensor/targeting ligand/molecular probe (Trade name) | Receptor/target (either on the cell or as toxins) |
|---|---|
| Anti-B4-blocked ricin | Mouse anti-CD19/ricin with the galactose binding site blocked |
| Denilelukin diftitox (Ontak ™) | Interleukin-2/diphtheria toxin fragment fusion protein |
| Galactosamine | Galactosamine receptors on hepatocytes |
| Folate | Folate receptor |
| Anti-ERBB2 (Herceptin ™) | ERBB2 receptor |
| Anti-CD20 (Rituxan ™) | CD20, B-cell surface antigen |

According to another aspect, the present invention also provides a kit comprising:
NIR-sensitive nanoparticle(s); and
one or more surfactant(s) according to any embodiment of the invention.

The surfactant(s) may be any surfactant which has already been described. The surfactant may be just one type of surfactant or a mixture of surfactants. The kit may further comprise a biomolecule. The biomolecule may be any drug within the scope of the present invention.

Having now generally described the invention, the same will be more readily understood through reference to the following examples which are provided by way of illustration, and are not intended to be limiting of the present invention.

EXAMPLES

Example 1

Synthesis of NIR-Sensitive Nanoparticles

Aqueous sodium sulfide ($Na_2S$) was used to reduce aqueous tetrachloroauric acid ($HAuCl_4$) to synthesise the NIR-sensitive nanoparticles (Zhou et al., 1994; Averitt et al., 1997; Ren and Chow, 2003). 1 mM of $Na_2S$ aged for a day was mixed with 2 mM of $HAuCl_4$ at S:Au molar ratios ranging from 0.5 to 0.9. The aging of $Na_2S$ was required due to the limited solubility of metal sulfides in water (Licht, 1988). These chemicals were purchased from Sigma Aldrich Corporation.

Synthesis of NIR-Sensitive Nanoparticle Complex

Anti-cancer drugs and other biomolecules can be loaded onto the NIR-sensitive nanoparticles by coating the particles with surfactants. These surfactants have functional groups that are reactive to the NIR-sensitive carriers (e.g. thiol groups) and anti-cancer drugs (e.g. carboxyl group). The surfactants used in the example were mercaptoacetic acid (MAA, $HSCH_2COOH$), mercaptopropionic acid (MPA, $HS(CH_2)_2COOH$) and mercaptoundecanoic acid (MUA, $HS(CH_2)_{10}COOH$) purchased from Sigma Aldrich Corporation. Upon completion of the synthesis of NIR-sensitive nanoparticles (colloids), MAA and MPA (which are water-soluble) were added directly into the reaction mixture at 100 mM. The insolubility of MUA in water necessitated the chemisorption of MUA in absolute ethanol. NIR-sensitive nanoparticles (colloids) were separated from the aqueous reaction mixture by centrifugation, and dispersed in 100 mM MUA in absolute ethanol. The nanoparticles (colloids) were dispersed in these surfactant solutions for 3 days, an estimated time for chemisorption to reach equilibrium.

Synthesis of Drug Loaded NIR-Sensitive Nanoparticles

The drug that was to be loaded on the NIR-sensitive nanoparticles was cisplatin (Sigma Aldrich Corporation). Excess surfactants were removed by centrifugation and the coated nanoparticles were dispersed in 1 mg/mL of aqueous cisplatin solutions after at least 3 washes. The adsorption of cisplatin on the coated nanoparticles was allowed to take place over 2 days. Excess cisplatin was removed by centrifugation. The drug-loaded colloids were washed at least 3 times and dispersed in water.

Characterisation Techniques

The UV-visible spectrum scans (400-1100 nm) of the colloidal solutions were taken using the Shimadzu spectrophotometer UV 1601 (Colloidal solutions is a general description that refers to both the modified and unmodified NIR-sensitive nanoparticles).

Transmission electron micrographs of samples on 400-mesh carbon-coated copper grids were taken using the JEOL 3010 transmission electron microscope (TEM) equipped with a LaB6 gun operating at an accelerating voltage of 300 kV.

Powder X-ray diffraction (XRD) patterns were obtained using the Bruker powder diffractometer (45 kV, 40 mA) with Cu K$\alpha$ radiation ($\lambda$=1.5406 Å). The XRD diffraction patterns were collected at $2\theta$=20° to 90° with a resolution of 0.02°. The Scherrer equation was used to determine the X-ray coherence length, crystallite grain size.

Fourier-transform infrared (FTIR) spectra were obtained with a Biorad FTS-60A/896 spectrometer. Nondestructive characterisation of the freeze-dried samples purged with helium can be performed using the MTEC model 200 photoacoustic cell. The spectrum scans were collected at a speed of 5 kHz for 400 to 4000 $cm^{-1}$ with a resolution of 4 $cm^{-1}$.

Thermogravimetric analysis (TGA) was conducted in helium using a Perkin-Elmer series 7 Thermal Analysis system at a ramp rate of 4° C./min from 30° C. to 900° C.

Zeta potential and light scattering measurements of the colloids dispersed in 0.1 M sodium phosphate ($NaPO_4$) buffers from pH 1 to 11 were taken using Malvern Instruments Zetasizer 2000 and Brookhaven Instruments ZetaPlus systems, respectively. The pH was adjusted using dilute hydrochloric acid (HCl) and sodium hydroxide (NaOH).

Chemical microanalysis of samples on 200-mesh carbon-coated copper grids was conducted using the VG HB603 scanning transmission electron microscope (STEM) operating at 250 kV, equipped with a field emission gun and wide-angle X-ray detector. The data was normalised with respect to copper.

Results and Discussion (A) Characterisation of NIR-Sensitive Nanoparticles

Figure 2:
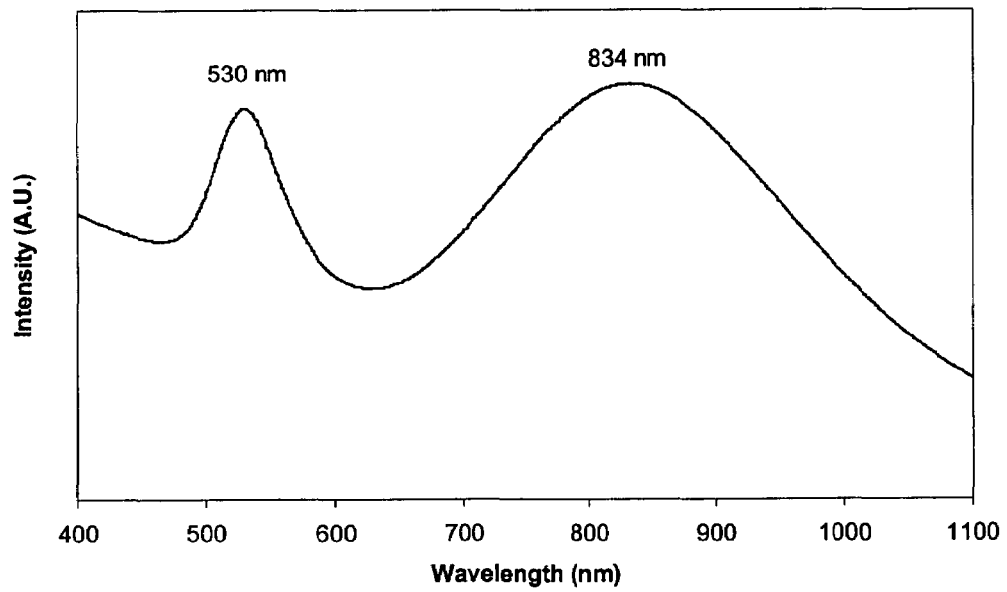
FIG. 2 shows a typical UV-visible spectrum of NIR-sensitive colloids.
Figure 3:
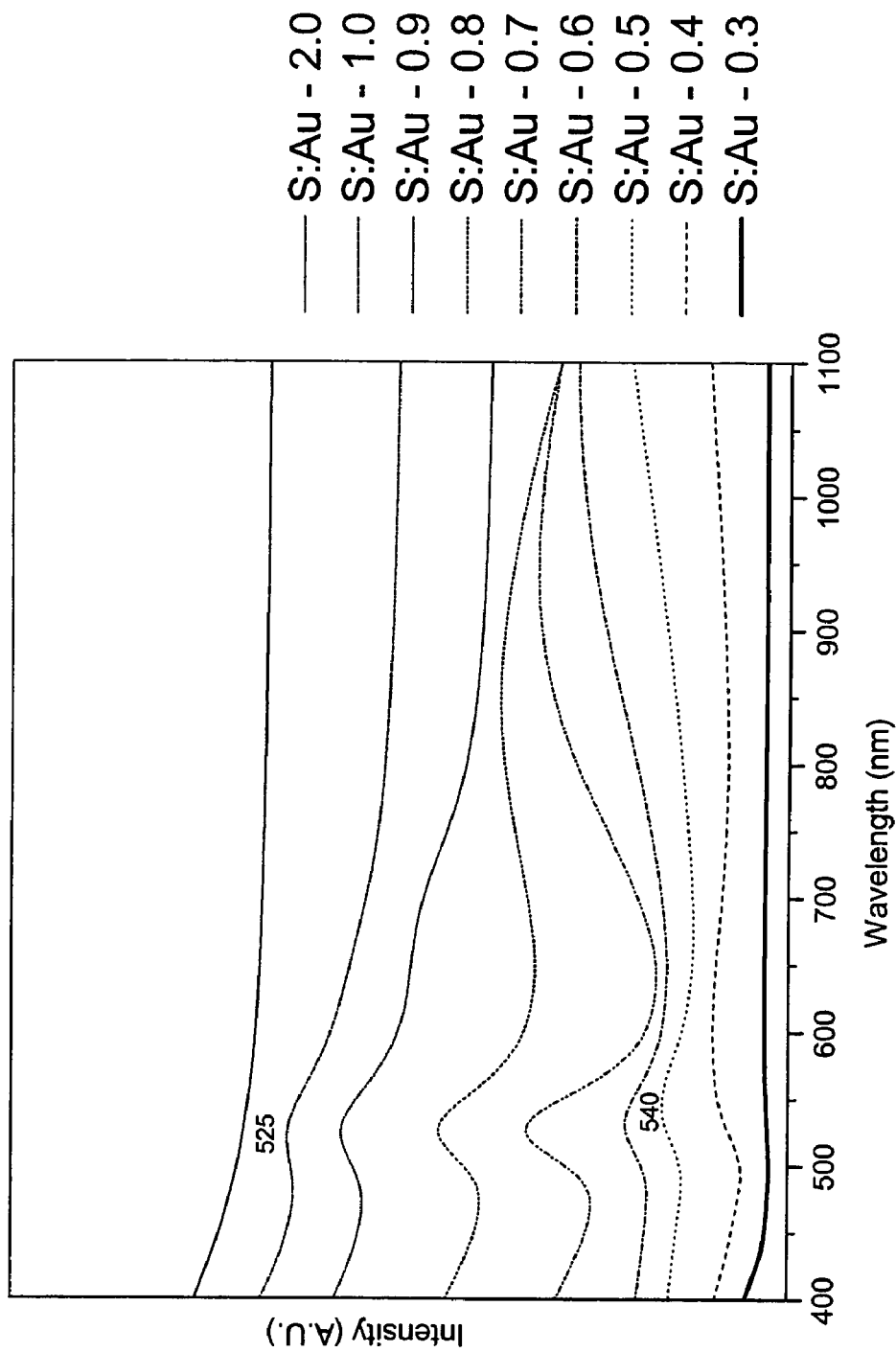
FIG. 3 shows the optical properties of the as-synthesized colloids with varying gold:sulfur precursor molar ratios

Preliminary analysis of the NIR properties of the colloids (NIR-sensitive nanoparticles) can be elucidated from the UV-visible spectra. From the light scattering and TEM data, the size distribution of the synthesised particles was found to be 30 to 50 nm. A typical UV-visible spectrum of the colloidal solution (FIG. 2) displayed peaks at two positions: 520-540 nm and, 650-1000 nm. The peak positions and relative peak intensities of the colloids depend on the S:Au molar ratios and mixing intensity during synthesis. The effect of S:Au precursor molar ratio on the optical properties is as illustrated in FIG. 3 and the elemental composition of the as-synthesized nanoparticles was determined using energy dispersive X-ray analysis (EDX) as shown in Table 2.

TABLE 2

Effect of Precursor Ratios of as synthesized nanoparticles, shaded region represent NIR-sensitive nanoparticles, $(Au_z)_{crystalline}$ $(Au_x\!-\!S_y)_{amorphous}$

| Precursor Molar Ratio | Au (at %) | | S (at %) | | $Au_{z+x}\!-\!S_y$ | |
|---|---|---|---|---|---|---|
| S:Au | Ave | Std. Dev | Ave | Std. Dev | z + x | y |
| 0.3 | 97.1 | 0.9 | 2.9 | 0.9 | 33.0 | 1 |
| 0.4 | 97.3 | 0.7 | 2.7 | 0.7 | 36.2 | 1 |
| 0.5 | 96.7 | 0.6 | 3.3 | 0.6 | 29.4 | 1 |
| 0.6 | 94.6 | 0.8 | 5.4 | 0.8 | 17.7 | 1 |
| 0.7 | 91.2 | 0.4 | 8.8 | 0.4 | 10.4 | 1 |
| 0.8 | 86.5 | 1.8 | 13.5 | 1.8 | 6.4 | 1 |
| 0.9 | 81.5 | 0.3 | 18.5 | 0.3 | 4.4 | 1 |
| 1.0 | 79.2 | 0.9 | 20.8 | 0.9 | 3.8 | 1 |
| 2.0 | 64.0 | 1.2 | 36.0 | 1.2 | 1.8 | 1 |

The first peak at 520-540 nm had previously been attributed to gold nanoparticles that were synthesized during the reduction of $HAuCl_4$ (Zhou et al., 1994; Averitt et al., 1997). Table 3 shows the characteristic peaks of gold nanoparticles synthesized using other reducing agents.

TABLE 3

Peak positions of spherical gold nanoparticles in aqueous solution (Daniel and Astruc, 2004)

| Particle Size (nm) | Peak Position (nm) |
|---|---|
| <2 | — |
| 9 | 517 |
| 15 | 520 |
| 22 | 521 |
| 48 | 533 |
| 99 | 575 |
| Bulk | — |

This had been attributed to the surface plasmon absorbance of gold nanoparticles (Daniel and Astruc, 2004).

Figure 4:
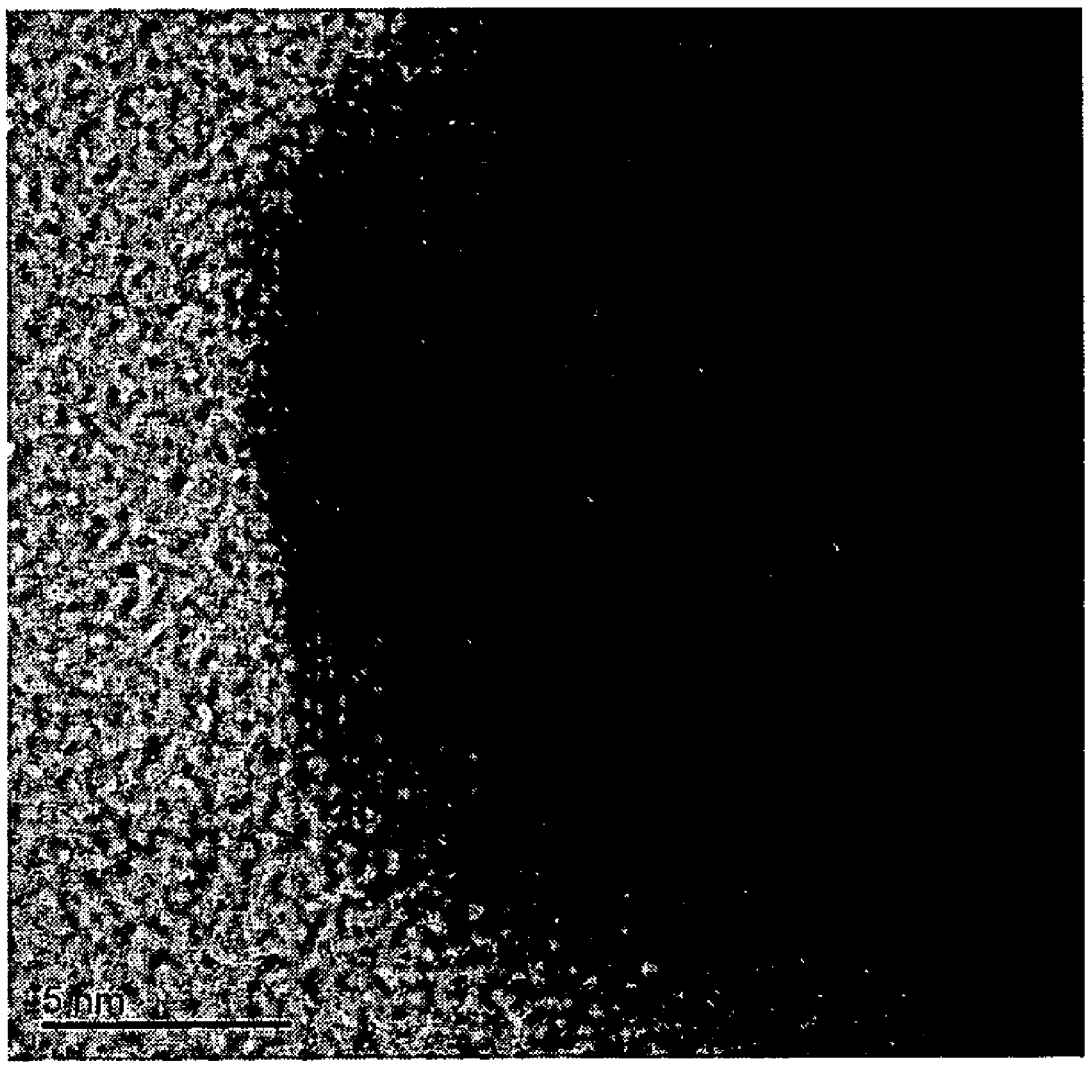
FIG. 4 is a High-resolution TEM micrograph of a typical NIR-sensitive nanoparticle.
Figure 5:
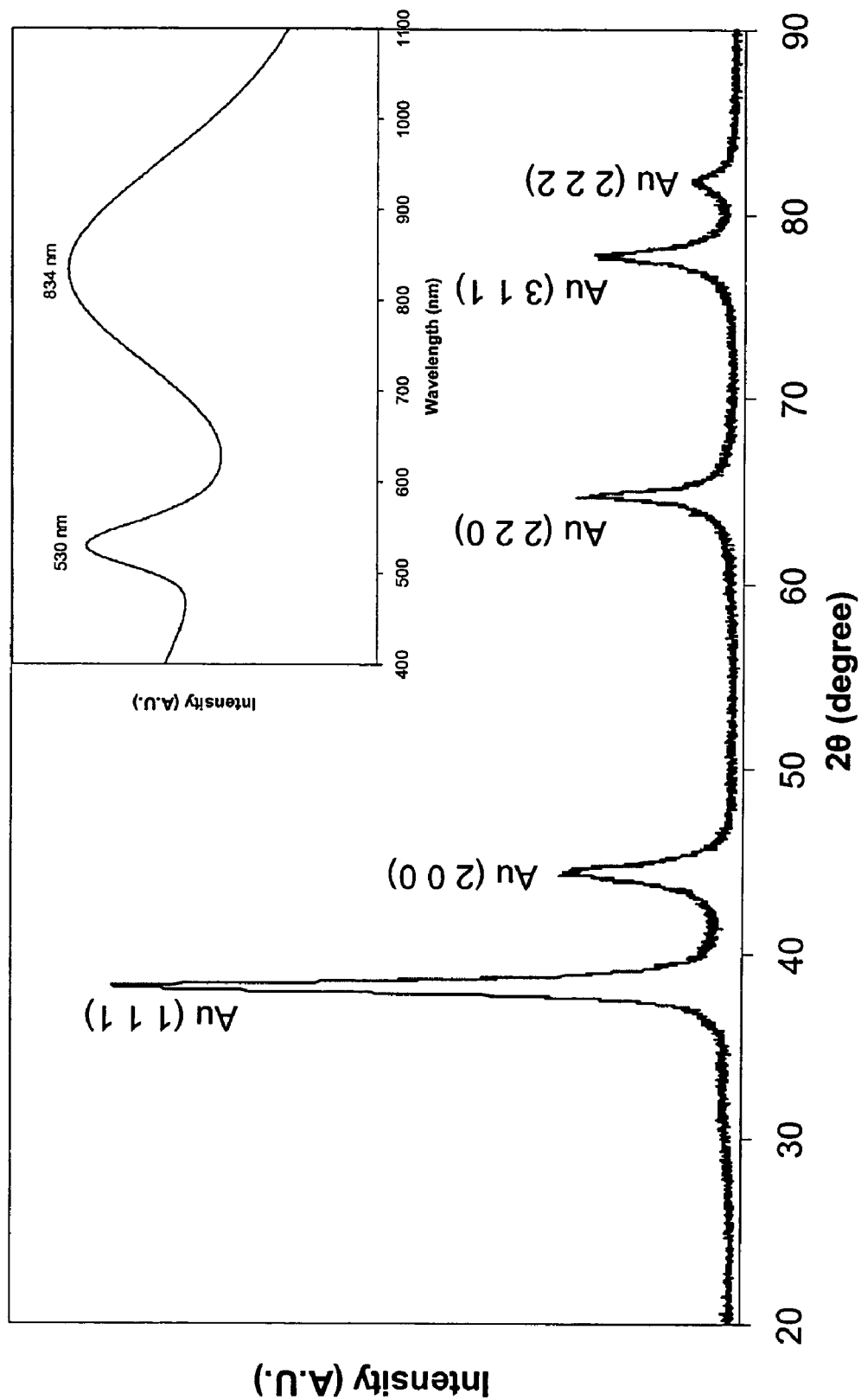
FIG. 5 shows XRD of freeze-dried particles with NIR properties.

The second peak located at the NIR region is not associated with gold (Daniel and Astruc, 2004) or gold sulfide nanoparticles (Morris et al., 2002). This NIR peak had been previously attributed to 5 nm crystalline gold (shell) and 30 nm gold sulfide (core) nanoshells (Zhou et al., 1994; Averitt et al., 1997). From the open literature, we had previously assumed a core-shell NIR nanoparticle though there was insufficient evidence to suggest that this existed (Ren and Chow, 2003). Our current data from high-resolution TEM (HRTEM) and powder XRD patterns suggested otherwise. HRTEM micrographs (FIG. 4) did not show any core-shell structures. The XRD pattern revealed the characteristic peaks of face-centered cubic (FCC) Au (FIG. 5), with an average crystallite size of ~12 nm. The calculated lattice parameter, $a_{o,\,calculated}$=4.076±0.006 Å is within 5% of the theoretical lattice parameter, $a_{o,\,theoretical}$=4.0786 Å of FCC gold (Swanson and Tatge, 1953). Using the strongest $Au_2S$ peak at 30.847° (Ishikawa et al., 1995) and assuming FWHM (Full Width at Half Maximum)=180°, the Scherrer equation estimated that $Au_2S$ will need to have a X-ray coherence length or crystallite size of <0.48 Å to elude XRD detection. Thus, it is unlikely that crystalline $Au_2S$ was present in the NIR-sensitive nanoparticles. Taking into account the atomic radius of S atoms (1.27 Å) and the radii of octahedral (0.604 Å) and tetrahedral (0.329 Å) interstices of FCC Au, it is not likely that S atoms can diffuse into the interstitial vacancies. The NIR-sensitive nanoparticles were likely to be nanocomposites of amorphous $Au_xS_y$ and crystalline Au. X-ray absorption fine structure (XAFS) of the nanoparticles will be used to further elucidate the composition and structure of the NIR-sensitive nanoparticles.

Figure 6:
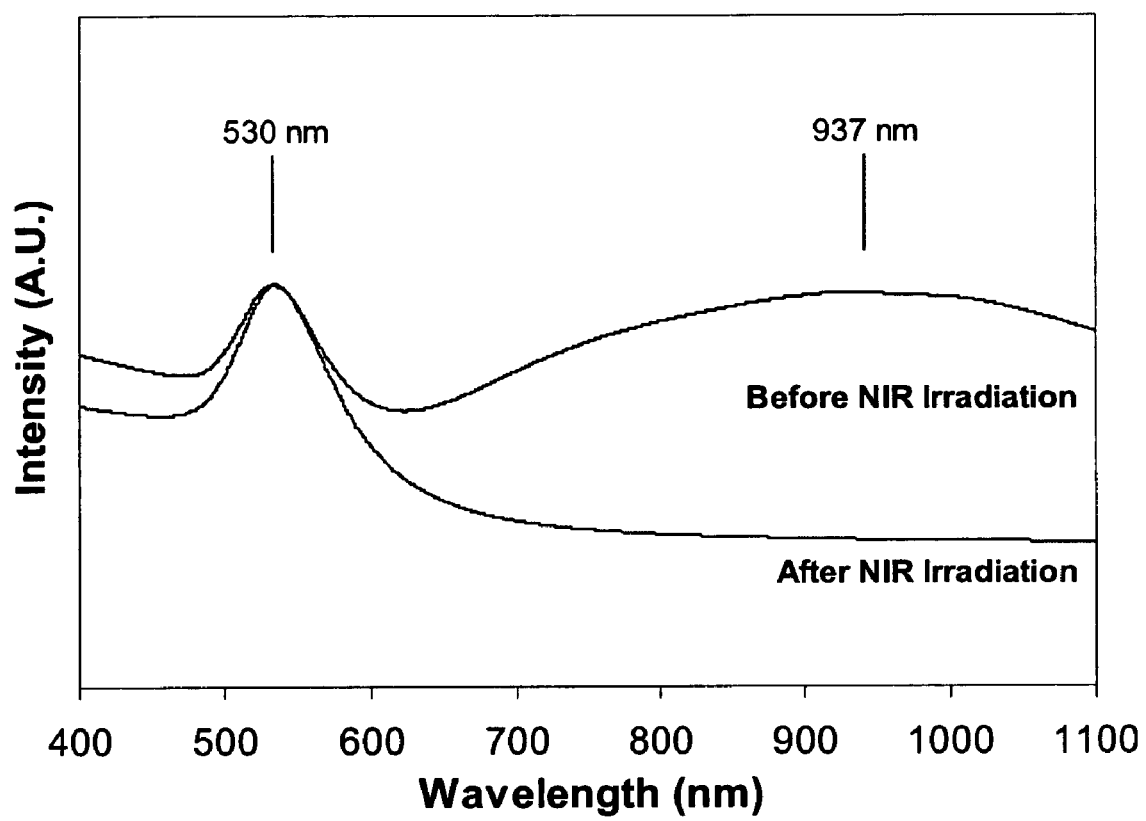
FIG. 6 shows the effect of NIR exposure on the optical properties of the NIR-sensitive nanoparticles.
Figure 7:
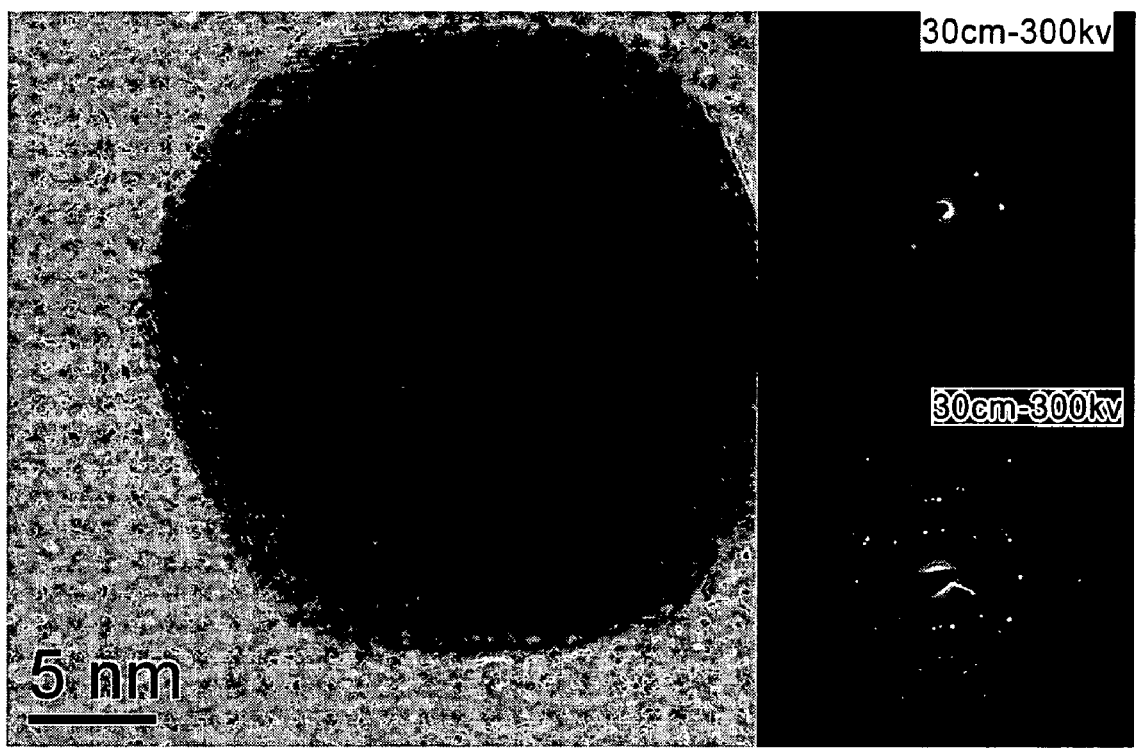
FIG. 7 is a High-resolution TEM micrograph of a typical NIR-sensitive nanoparticle before NIR exposure.
Figure 8:
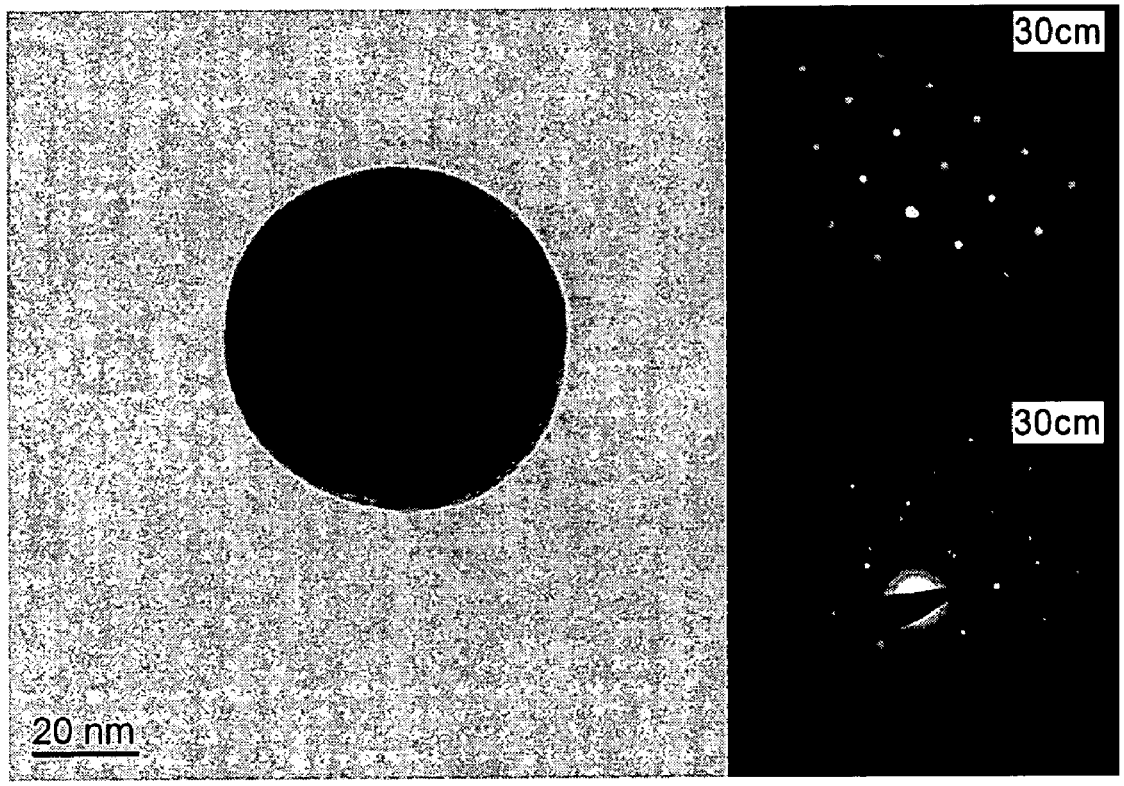
FIG. 8 is a High-resolution TEM micrograph of a typical NIR-sensitive nanoparticle after NIR exposure.
Figure 9:
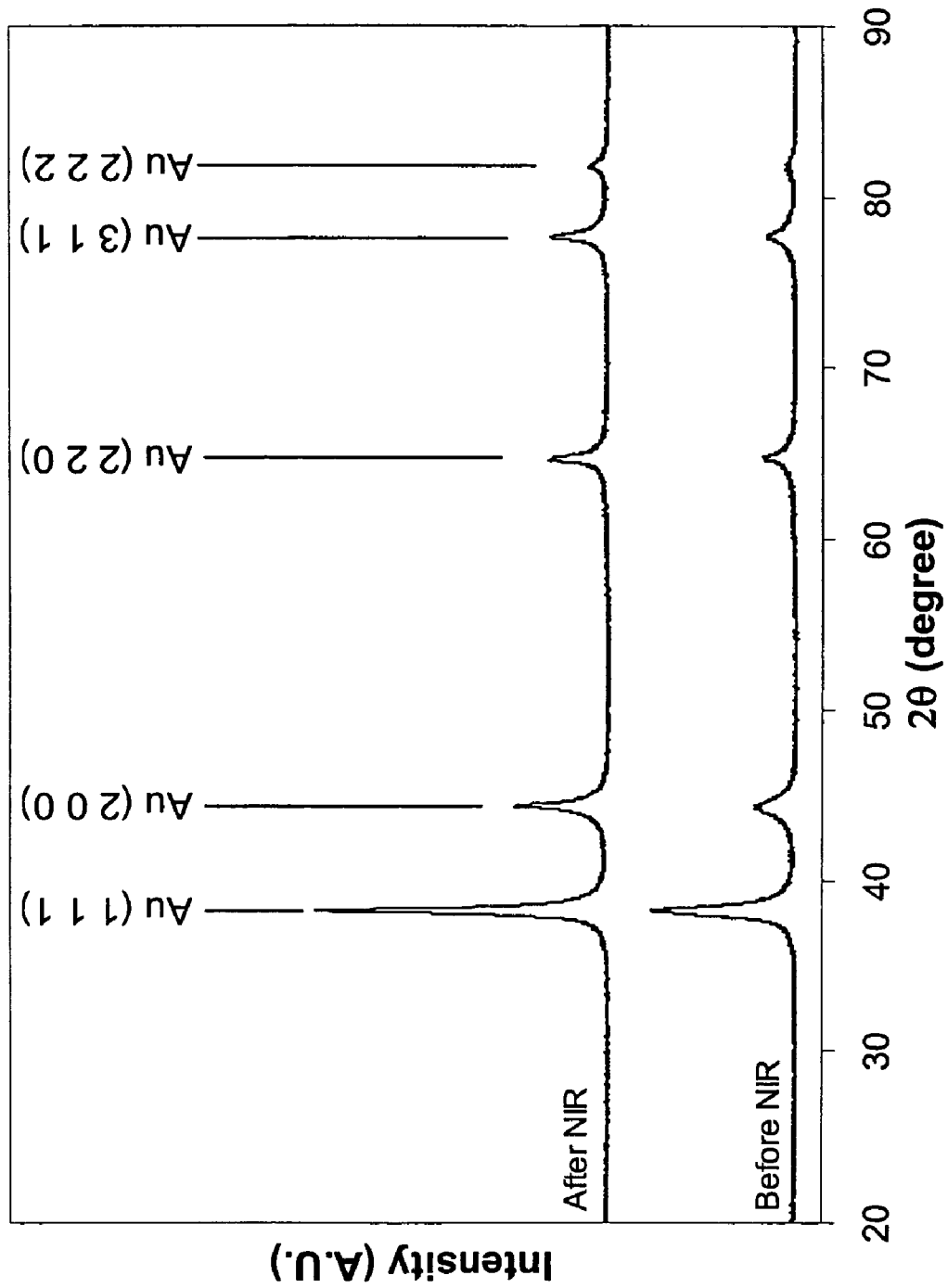
FIG. 9 shows XRD of NIR-sensitive nanoparticles before and after NIR exposure.

Upon exposure to NIR irradiation (30 min at 1064 nm, 15 Hz, 50 mJ/pulse, 7 ns/pulse), the optical properties of the NIR-sensitive nanoparticles are significantly changed as illustrated in FIG. 6. Besides this significant change in optical properties, HRTEM micrographs of the nanoparticles, as illustrated in FIGS. 7 and 8 shows that the nanoparticles adopted a more spherical morphology upon NIR exposure. Analysis of the XRD data (FIG. 9) of the nanoparticles, as presented in Table 4, shows that photoannealing of the crystalline Au grains was most likely to have occurred. The above mentioned evidence indicates that a photophysical change of the nanoparticles was effected by the NIR exposure.

TABLE 4

NIR effects on X-ray coherence length (grain size) and lattice strain

| | X-ray Coherence Length, grain size (nm) | Lattice Strain |
|---|---|---|
| Before NIR | 10 | $7.6 \times 10^{-4}$ |
| After NIR | 30 | $5.3 \times 10^{-4}$ |

† Using integral breadth method for (1 1 1) and (2 2 2)

(B) Characterisation of Surface-Modified Nanoparticles

The difference in chain length alters the physical and chemical properties (e.g. water-solubility) of the surfactants. MAA, MPA and MUA were used to investigate the effect of surfactant chain length on the interfacial properties of surface-modified colloids (NIR-sensitive nanoparticle complex). The use of different surfactants to adjust surface reactivity can potentially allow the manipulation of drug loading and release.

Figure 10:
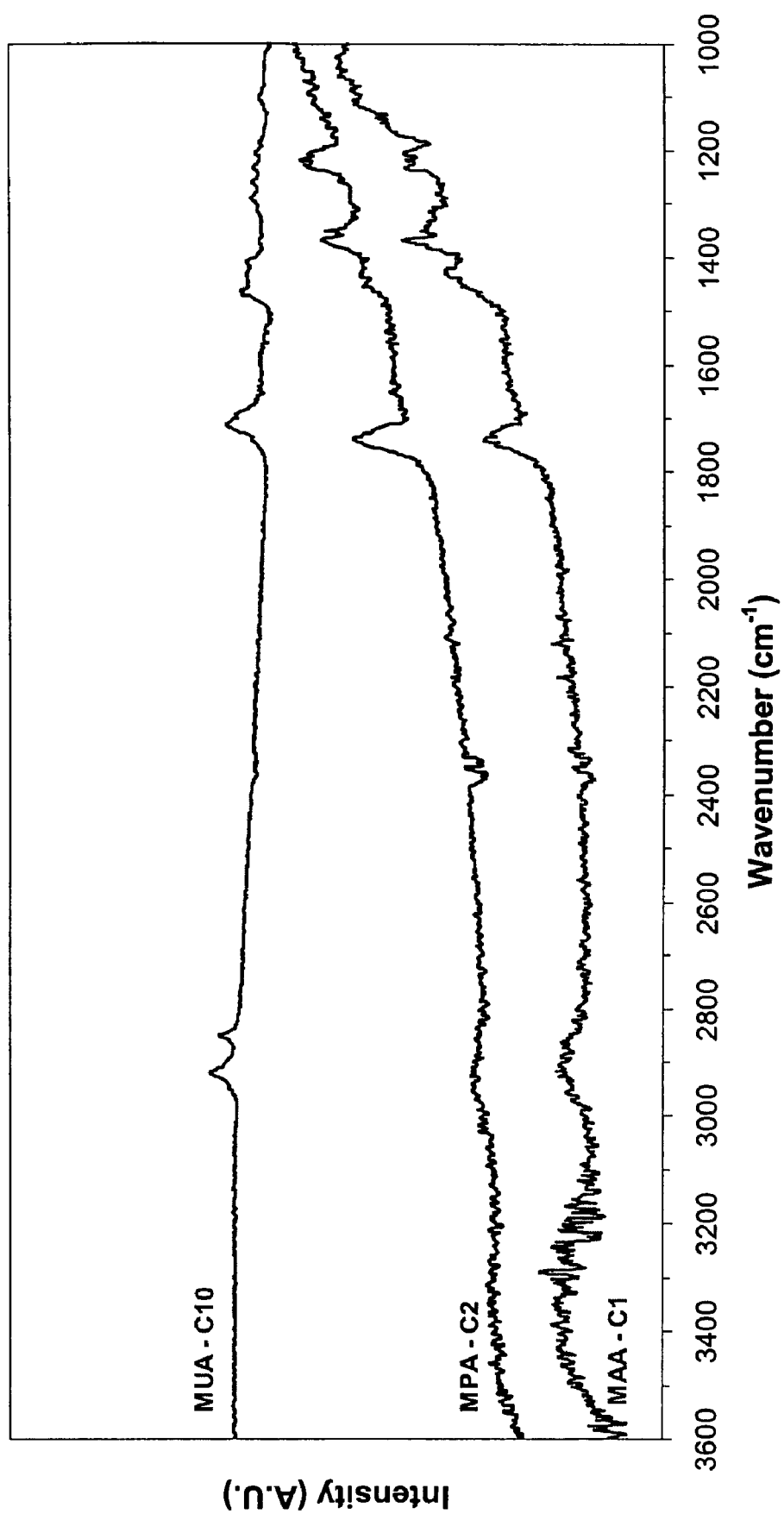
FIG. 10 shows FTIR spectra of surface-modified colloids.
Figure 11:
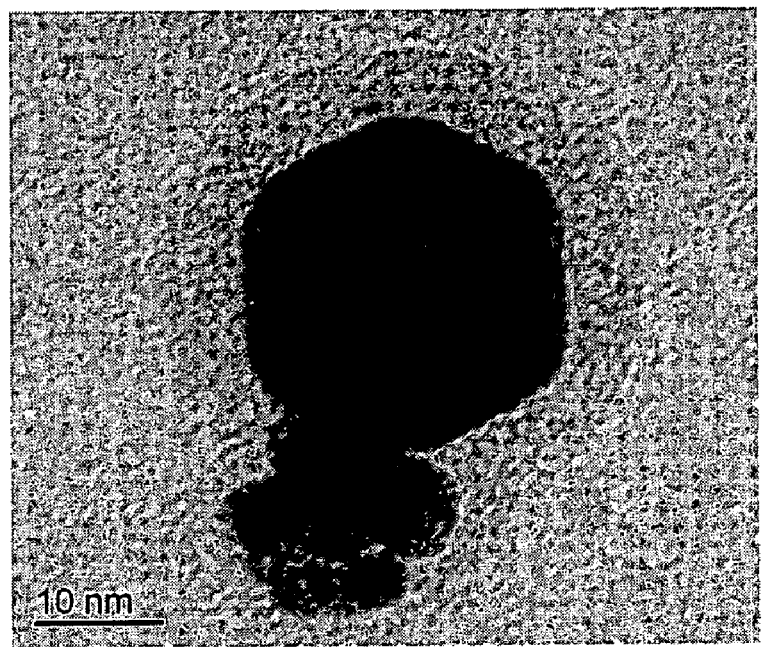
FIG. 11 shows TEM micrograph of MUA-modified colloid.
Figure 12:
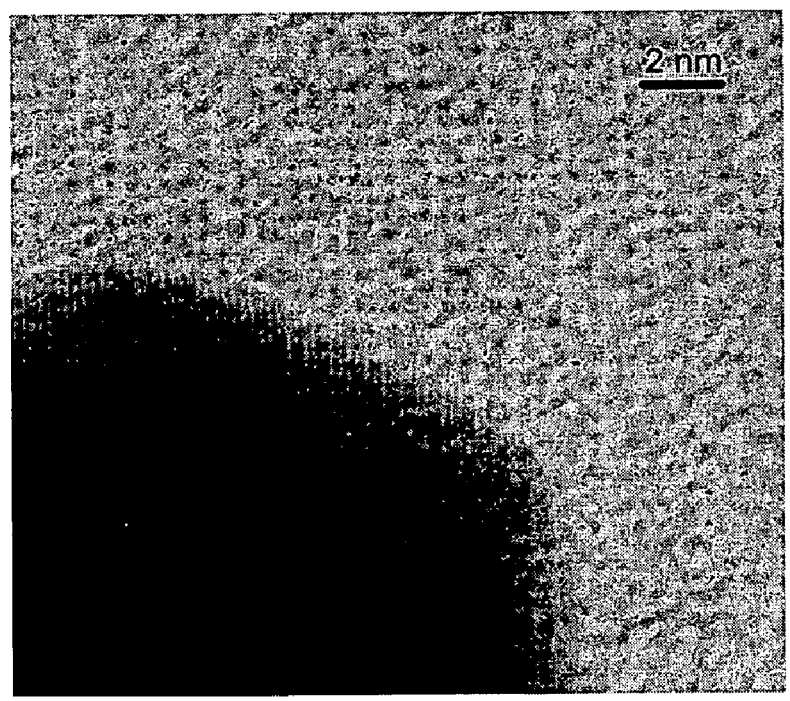
FIG. 12 is a High-resolution TEM micrograph of MUA-modified colloid.

The FTIR spectra of the freeze-dried colloids shown in FIG. 10 indicated the presence of the surfactants on the NIR-sensitive nanoparticles (colloids). Peaks found at ~1200 $cm^{-1}$, ~1400 $cm^{-1}$, ~1700 $cm^{-1}$ and ~2900 $cm^{-1}$ verified the presence of: CO; $COO^-$ and $CH_2$; COOH; and $CH_2$, respectively, which were characteristic of the surfactants used. TEM micrographs in FIG. 11 and FIG. 12 showed a 5-nm coating of MUA surfactant around a NIR-sensitive nanoparticle (colloid). Results obtained from the TGA of the freeze-dried particles in Table 5 showed that more of the short chain surfactants were adsorbed onto each NIR-sensitive nanoparticle.

TABLE 5

Amount of ligand adsorbed and its thermal properties

| Surface ligand | Ave. Absorbed (nmol/mg) | Decomposition Temp. (° C.) |
|---|---|---|
| MAA - C1 | 0.14 ± 0.01 | ~150 |
| MPA - C2 | 0.16 ± 0.01 | ~150 |
| MUA - C10 | 0.10 ± 0.03 | ~200 |

Considering that the available photon energy at 1064 nm (1.16 eV) is insufficient to break the bonds of the surfactant (Table 6), drug release from the NIR-sensitive nanoparticle complex will likely be a thermally driven event. Thus, the difference in the decomposition temperature of surfactants from the TGA data suggested that drug release kinetics was likely to be different. NIR-sensitive nanoparticles (colloids) modified with the short-chain surfactants, MAA and MPA, to form NIR-sensitive nanoparticle complexes also appeared to have a higher surface energy than those modified with the long-chain surfactant, MUA. The increased entanglement of MUA and the interactions between MUA and Au reduced the effective colloidal surface energy, and consequently increased the MUA decomposition temperature.

TABLE 6

Dissociation energy of chemical bonds (Vogel and Venugopalan, 2003)

| Molecular Bond | Dissociation Energy (eV) |
|---|---|
| C=O | 7.5 |
| C=C | 6.4 |
| O—H | 4.8 |
| C—H | 4.3 |
| N—H | 4.1 |
| C—O | 3.6 |
| C—C | 3.6 |
| S—H | 3.5 |
| C—N | 3.0 |

Figure 13:
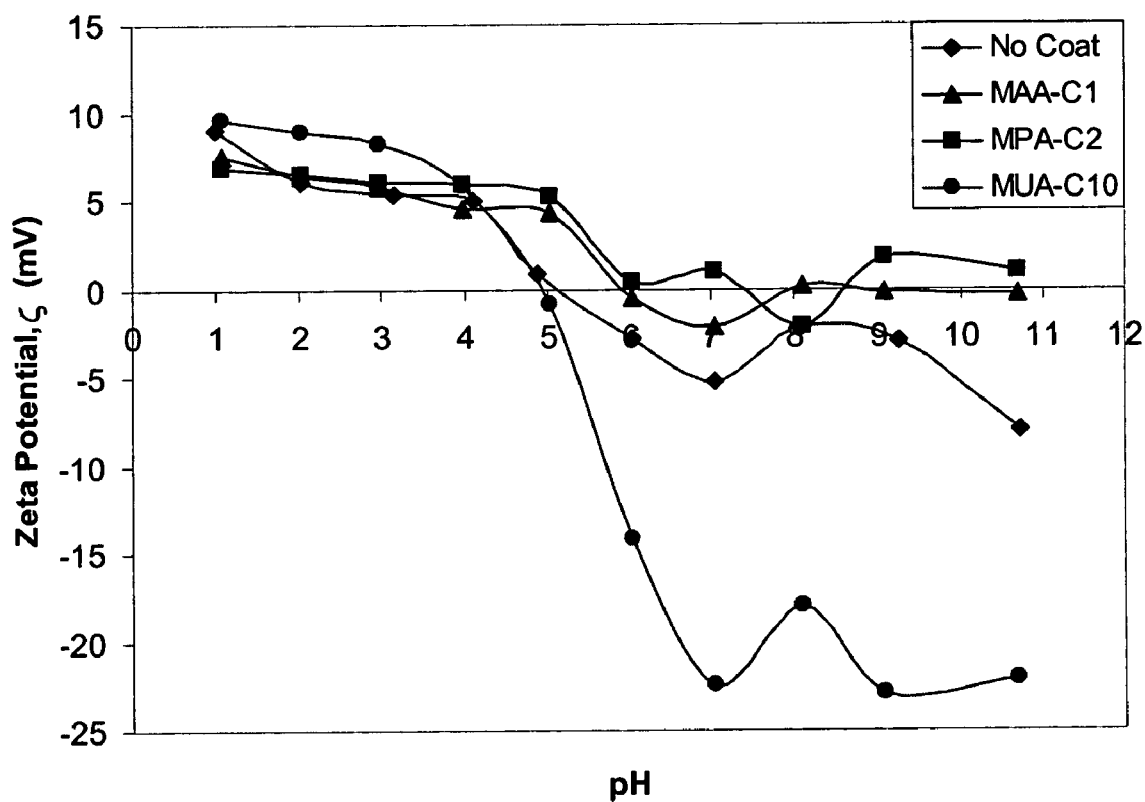
FIG. 13 shows a zeta potential of colloids in 0.1 M $NaPO_4$.

The surface characteristics of the colloids were investigated using zeta potential and light scattering techniques (P. C. Hiemenz, R. Rajagopalan, Principles of Colloid and Surface Chemistry, Marcel Dekker, Inc., Third edition, 1997). Zeta potential data (FIG. 13) obtained for MUA-modified colloids showed that there was little difference in the isoelectric point of the modified (NIR-sensitive nanoparticle complex) and uncoated (NIR-sensitive nanoparticle) colloids. This can be associated with the pKa of MUA, which was calculated to be about 4.78±0.20 (calculated using Advanced Chemistry Development (ACD) Software Solaris V4.67). MUA-modified colloids (NIR-sensitive nanoparticles with MUA adsorbed onto the nanoparticles) had a higher surface charge (~20 mV) than the uncoated (NIR-sensitive nanoparticles) colloids (~7 mV) from pH 6 to 10. This can be attributed to the dissociation of the carboxylic acid groups, COOH→COO$^-$, on MUA.

Figure 14:
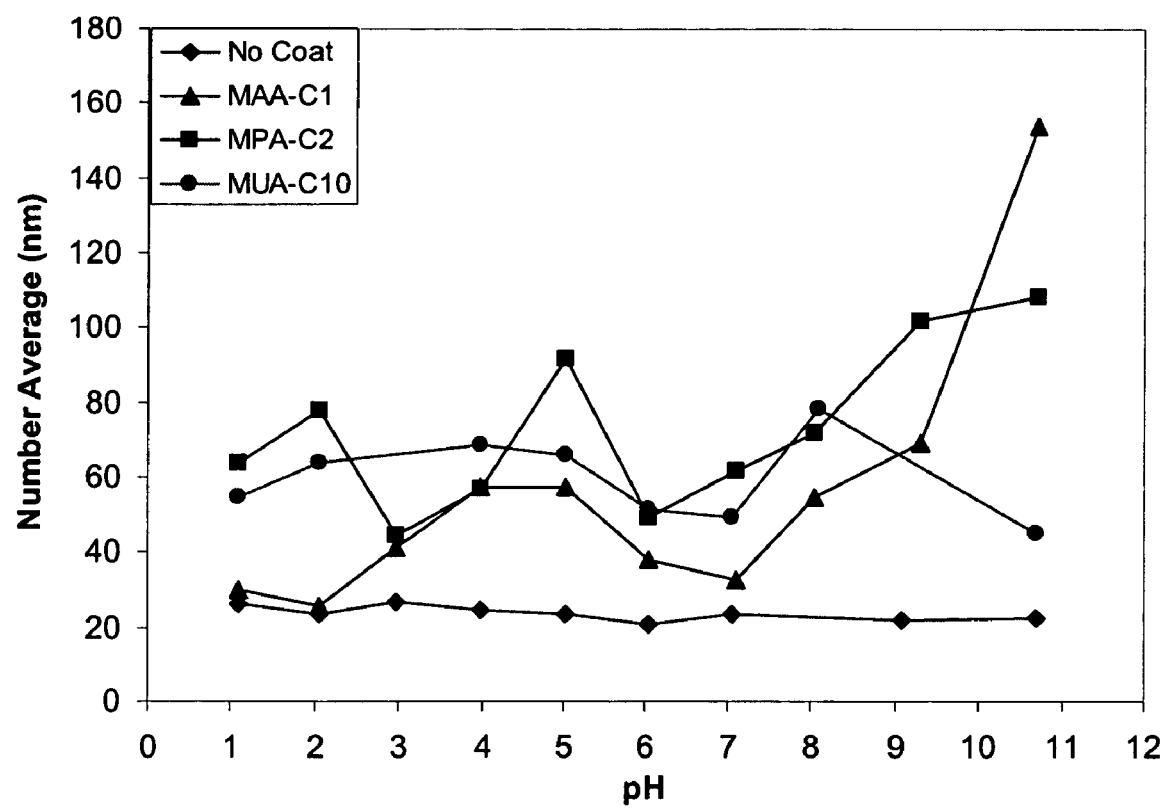
FIG. 14 shows light scattering of colloids in 0.1 M $NaPO_4$.

For MAA- and MPA-modified colloids (i.e. NIR-sensitive nanoparticle complex, there was no observed isoelectric point. The zeta potential of these modified colloids was about zero from pH 6 to 10. This was most likely due to the formation of flocs induced by the interactions of the COO$^-$ on the surfactant and Na$^+$ in the buffer. From FIG. 14, light scattering techniques that measured the effective hydrodynamic diameter of colloidal solutions indicated that flocculation was likely in MAA- and MPA-modified colloids. On the other hand, uncoated and MUA-modified colloids had relatively constant diameters, showing no signs of flocculation. Since flocculation is a reversible and dynamic process, it should be noted that each data point was taken at the same time point (~30 to 40 min) after the dispersion of colloids in buffers. The zeta potential and light scattering data suggested that MAA- and MPA-modified colloids were more reactive due to its higher surface energy than MUA-modified colloids, as in agreement with the TGA data.

(C) Characterisation of Drug-Loaded NIR-Sensitive Nanoparticle Complex

Figure 15:
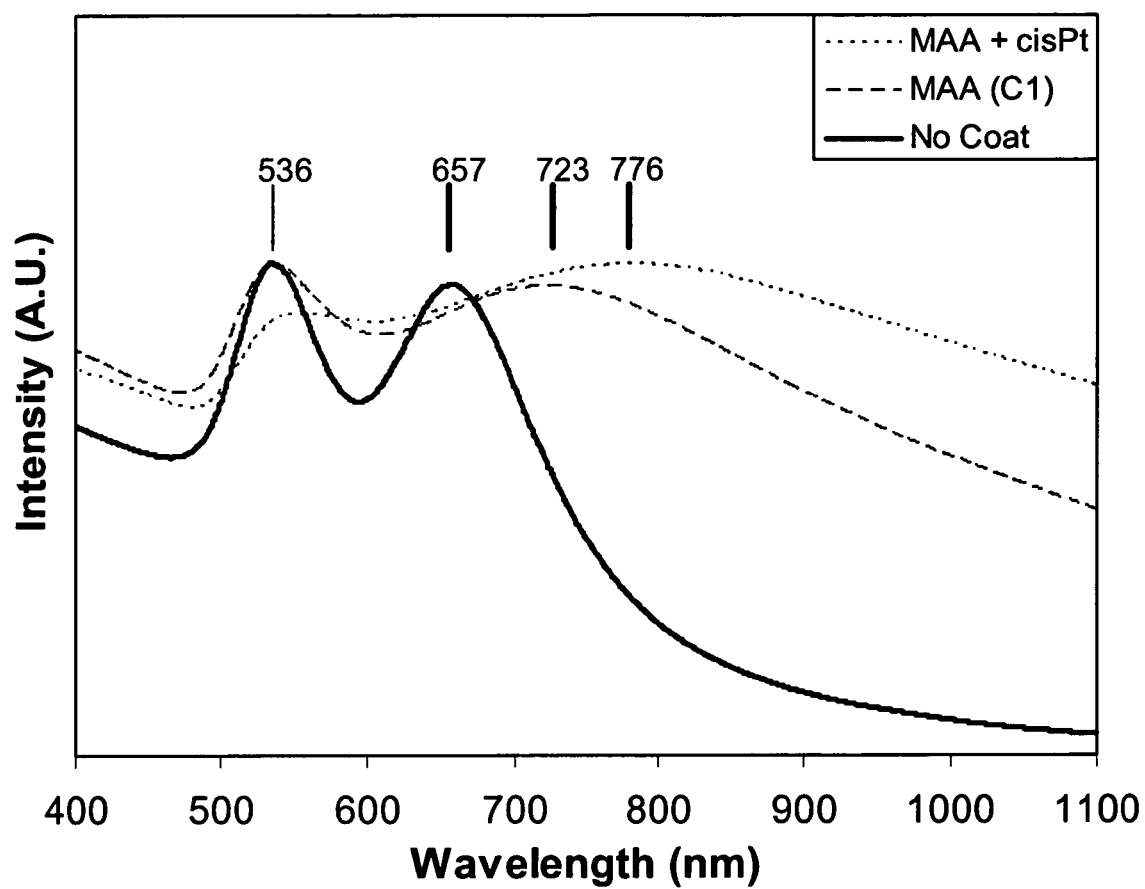
FIG. 15 shows optical properties of uncoated colloids and surface-modified (MAA and MAA+cisplatin) colloids.
Figure 16:
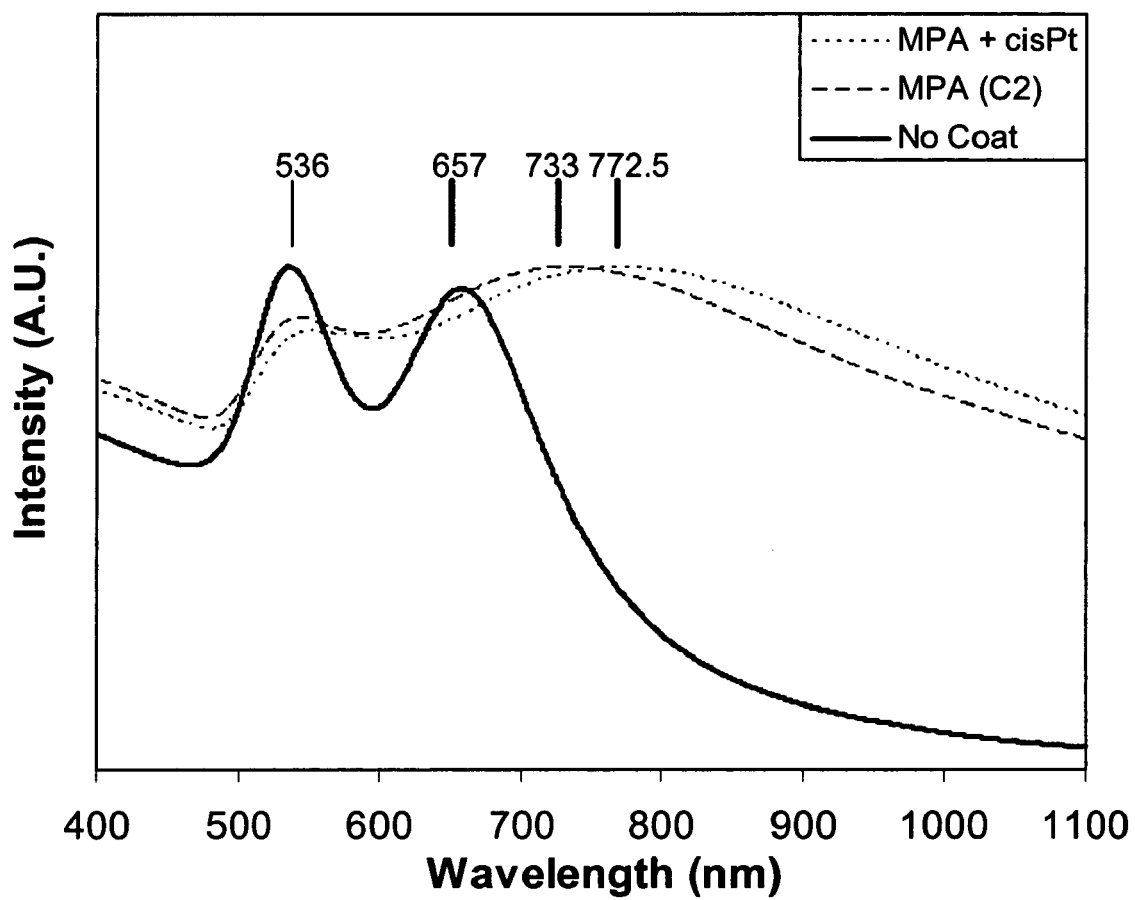
FIG. 16 shows optical properties of uncoated colloids and surface-modified (MPA and MPA+cisplatin) colloids.
Figure 17:
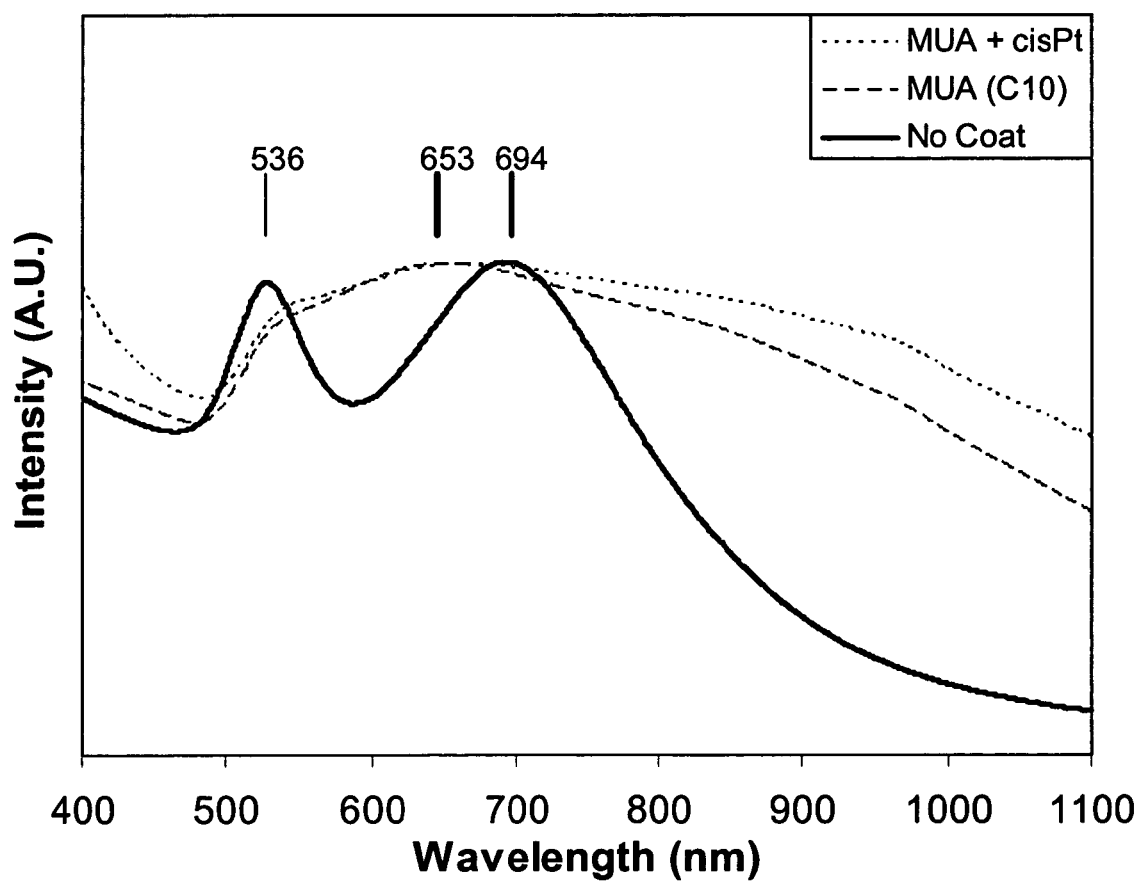
FIG. 17 shows optical properties of uncoated colloids and surface-modified (MUA and MUA+cisplatin) colloids.

Preliminary analysis of the UV-visible spectrum of the drug loaded NIR-sensitive colloids (nanoparticles) indicated a shift in the second peak in the NIR region to higher wavelengths after each modification. The results are shown in FIGS. 15, 16 and 17. This was likely to be caused by the changes in the size, surface and interfacial properties after the surface modification of the NIR-sensitive nanoparticles (colloids) by the surfactants adsorbed onto the surface of the nanoparticles. However, this was inconsequential to the suggested application of NIR-sensitive drug release, since the second peak remains in the NIR region.

Figure 18:
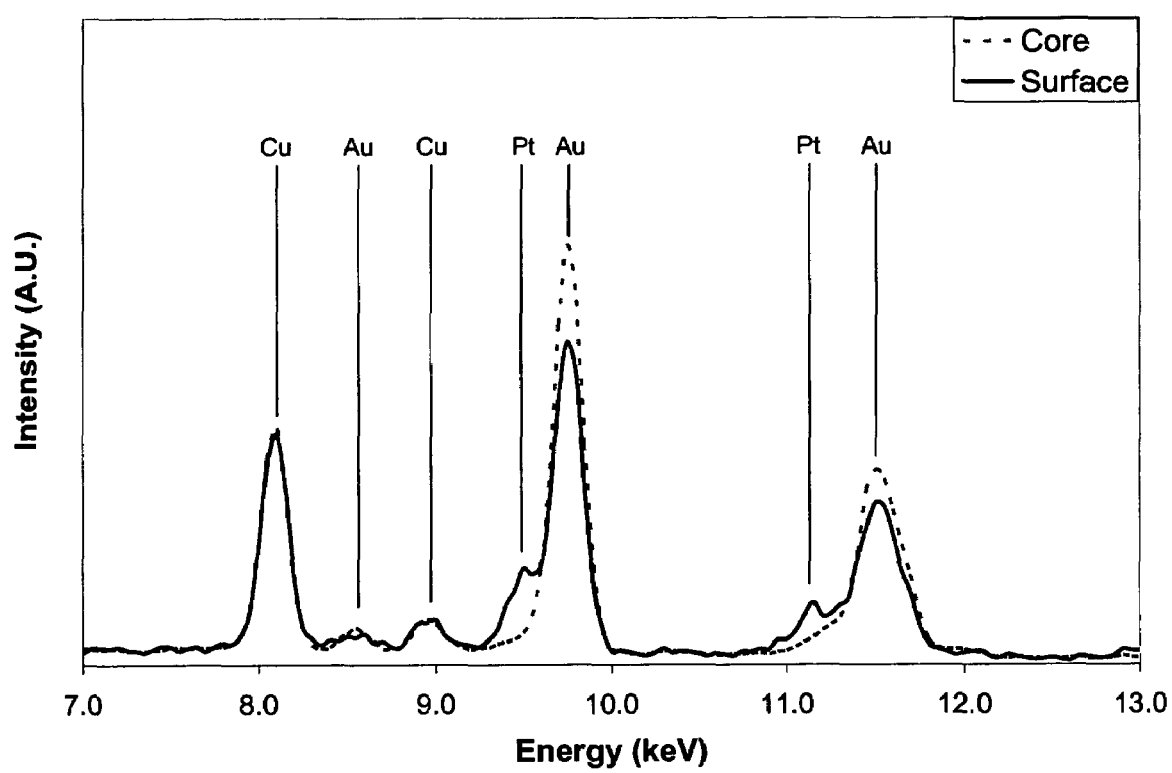
FIG. 18 shows EDX spectra of drug-loaded MAA-modified colloids.
Figure 19:
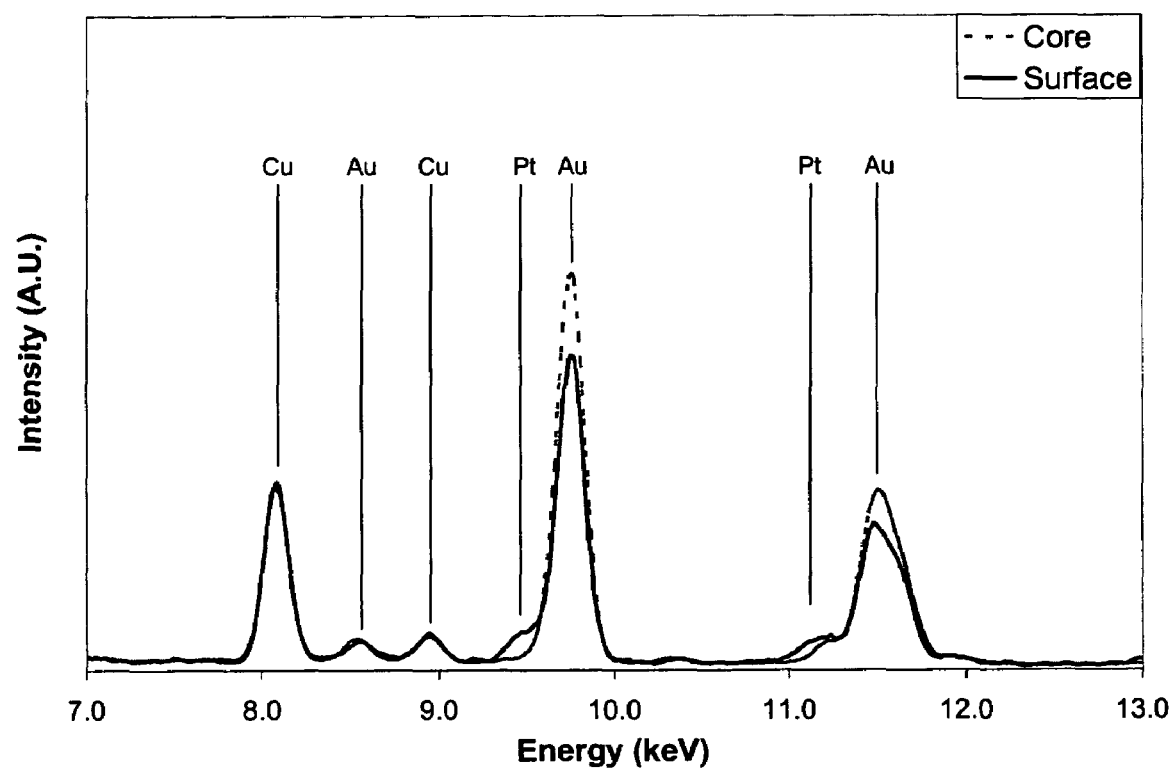
FIG. 19 shows EDX spectra of drug-loaded MPA-modified colloids.
Figure 20:
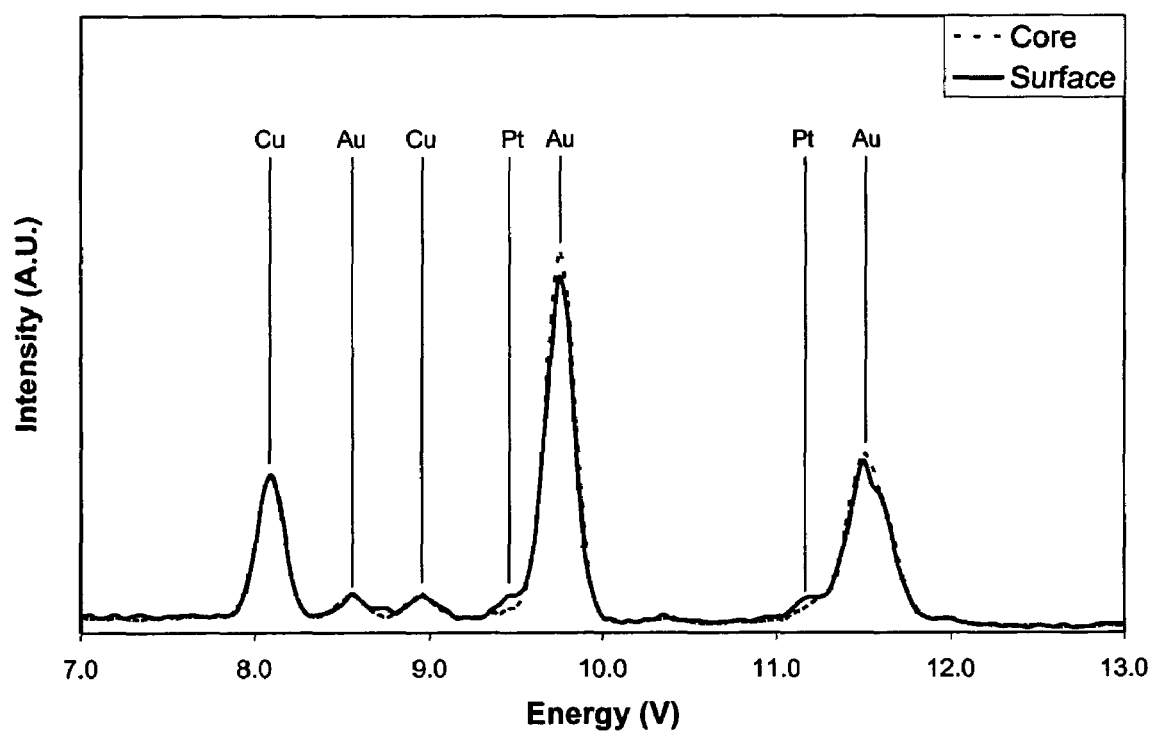
FIG. 20 shows EDX spectra of drug-loaded MUA-modified colloids.

Table 7 shows the chemical microanalysis of samples of drug loaded NIR-sensitive nanoparticle complex using energy dispersive X-ray analysis (EDX). The EDX data suggested that more of the anti-cancer drug, cisplatin, was loaded onto the MAA- and MPA-modified colloids than the MUA-modified colloids. The EDX spectra of drug-loaded MAA-, MPA- and MUA-modified nanoparticles are shown in FIGS. 18, 19 and 20, respectively. Additional work is currently underway to quantitatively determine the drug loading on the different surface-modified particles using either high-performance liquid chromatography or UV-visible absorption techniques by analysing the supernatant fraction after drug adsorption onto the particles.

TABLE 7

Total peak area of Au and Pt at 7-13 keV$^†$

| Element | MAA | | MPA | | MUA | |
|---|---|---|---|---|---|---|
|  | Core | Surface | Core | Surface | Core | Surface |
| Au | 86.58 | 72.92 | 119.88 | 84.91 | 190.91 | 155.14 |
| Pt | — | 24.00 | 4.07 | 23.31 | — | 21.31 |
| Pt (surf):Au (surf) | | 0.33 | | 0.27 | | 0.14 |

$^†$Peak area was obtained after peak fitting using OrginPro 7.

(Peak area are Arbitrary Units, with reference to the figures as shown in the brief description of the figures section).

Example 2

Modifications of the Example 1

In the above example, it can be concluded from HRTEM and XRD results that the NIR-sensitive properties were not likely to be caused by the formation of a crystalline structure of 5 nm Au (shell) and 30 nm Au$_2$S (core) as previously suggested (Zhou et al., 1994; Averitt et al., 1997; Ren and Chow, 2003). The previous assumption made about the presence of a core-shell NIR-sensitive particle (Ren and Chow, 2003) is no longer enabling in this work. These NIR-sensitive particles were more likely to be nanocomposites of crystalline Au and amorphous Au$_x$S$_y$, (Au$_z$)$_{crystalline}$ (Au$_x$—S$_y$)$_{amorphous}$. In addition, the current evidence suggests that the NIR-sensitive nanoparticles will undergo a photophysical change upon NIR exposure.

In addition, a method to manipulate drug loading and release by using different surface ligands has been suggested. MAA and MPA surface-modified colloids were more reactive than the MUA-modified colloids. This has enabled the increase in drug loading onto the colloids. Furthermore, with the difference in thermal properties, it is likely that drug release can be manipulated using surfactants with different chain lengths. It has previously been demonstrated that an anti-cancer drug such as cisplatin can be released using NIR light at 1064 nm at 100 mJ/pulse and a pulse duration of 7 ns at 10 Hz (Ren and Chow, 2003). The energy of the laser beam may be varied to study the photothermal effects on the drug release kinetics.

REFERENCES

Allen, T. M., Ligand-targeted therapeutics in anticancer therapy, *Nat Rev Cancer* 2002, 2, 750.

Averitt, R. D., Sarkar, D., Halas, N. J., Plasmon resonance shifts of Au-coated $Au_2S$ nanoshells: insight into multicomponent nanoparticle growth, *Phys Rev Lett* 1997, 78, 4217.

Daniel, M.-C., Astruc, D., Gold nanoparticles: assembly, supramolecular chemistry, quantum-size-related properties, and applications toward biology, catalysis, and nanotechnology, *Chem Rev* 2004, 104, 293.

Dolmans, D. E. J. G. J., Fukumura, D., Jain, R. K., TIMELINE: Photodynamic therapy for cancer, *Nat Rev Cancer* 2003, 3, 380.

Sato, S., et al., Nanosecond, high-intensity pulsed laser ablation of myocardium tissue at the ultraviolet, visible, and near-infrared wavelengths: in-vitro study, *Lasers Surg Med* 2001, 29, 464.

Sershen, S., West, J., Implantable, polymeric systems for modulated drug delivery, *Adv Drug Del Rev* 2002, 54, 1225.

Swanson, H. E., Tatge, E., Standard x-ray diffraction powder patterns, *National Bureau of Standards Circular* 1953, 539, 95.

Vogel, A., Venugopalan, V., Mechanisms of pulsed laser ablation of biological tissues, *Chem Rev* 2003, 103, 577.

Weissleder, R., A clearer vision for in vivo imaging, *Nat Biotechnol* 2001, 19, 316.

Zhou, H. S., Honma, I., Komiyama, H., Controlled synthesis and quantum-size effect in gold-coated nanoparticles, *Phys Rev B* 1994, 50, 12052.

SEQUENCE LISTING

```
<160> NUMBER OF SEQ ID NOS: 1

<210> SEQ ID NO 1
<211> LENGTH: 9
<212> TYPE: PRT
<213> ORGANISM: Murine Laminin (fragment 925-933)

<400> SEQUENCE: 1

Cys Asp Pro Gly Tyr Ile Gly Ser Arg
1               5
```

Frangioni, J. V., In vivo near-infrared fluorescence imaging, *Curr Opin Chem Biol* 2003, 7, 626.

Hiemenz P. C., Rajagopalan R., Principles of Colloid and Surface Chemistry, Marcel Dekker, Inc, 1997 Third Edition.

Hirsch, L. R., Jackson, J. B., Lee, A., Halas, N. J., West, J. L., A whole blood immunoassay using gold nanoshells, *Anal Chem* 2003, 75, 2377.

Hirsch, L. R., et al., Nanoshell-mediated near-infrared thermal therapy of tumors under magnetic resonance guidance, *Proc Natl Acad Sci USA* 2003, 100, 13549.

Ishikawa, K., Isonaga, T., Wakita, S., Suzuki, Y., Structure and electrical properties of $Au_2S$, *Solid State Ionics* 1995, 79, 60.

Kamat P. V., Photophysical, Photochemistry and Photocatalytic Aspects of Metal Nanoparticles, *J. Phys. Chem. B* 2002, 106, 7729.

Licht, S., Aqueous solubilities, solubility products and standard oxidation-reduction potentials of the metal sulfides, *J Electrochem Soc* 1988, 135, 2971.

Morris, T., Copeland, H., Szulczewski, G., Synthesis and characterization of gold sulfide nanoparticles, *Langmuir* 2002, 18, 535.

Oldenburg, S. J., Averitt, R. D., Westcott, S. L., Halas, N. J., Nanoengineering of optical resonances, *Chem Phys Lett* 1998, 288, 243.

Panyam, J., Labhasetwar, V., Biodegradable nanoparticles for drug and gene delivery to cells and tissue, *Adv Drug Del Rev* 2003, 55, 329.

Ren, L., Chow, G. M., Synthesis of NIR-sensitive Au—$Au_2S$ nanocolloids for drug delivery, *Mater Sci Eng, C* 2003, 23, 113.

What is claimed is:

1. A Near Infrared Sensitive (NIR-sensitive) nanoparticle complex comprising a NIR-sensitive nanoparticle and surfactant(s) adsorbed on the nanoparticle, wherein the surfactant is at least one surfactant selected from:

(a) 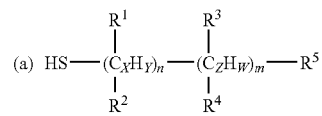

wherein X=1-9; Y=0-9; n=0-9; Z=1-9; W=0-9; m=0-9;
each of $R^1$, $R^2$, $R^3$ and $R^4$ independently, if present, is H, substituted or unsubstituted $C_1$-$C_6$ alkyl, substituted or unsubstituted $C_1$-$C_6$ aryl, HS, COOH, $NH_2$ or OH;
$R^5$ is COOH, $NH_2$ or OH;
with the proviso that n+m is <10;

(b) an amino acid having the structure in (a), wherein X=1; Y=2; Z=1; W=1; $R^1$, $R^2$ and $R^4$ are not present; $R^3$ is $NH_2$; and $R^5$ is COOH; or (c) a peptide, wherein the peptide comprise at least one amino acid (b) and consisting of a sequence of SEQ ID NO:1.

2. The nanoparticle complex of claim 1, wherein the surfactant(s) is at least one or a mixture of the following:

(i) a surfactant, comprising thiol and carboxylic acid functional groups, selected from mercaptosuccinic acid, mercaptobenzoic acid, penicillamine, mercaptopropionyl glycine, thioldiacetic acid, thiodipropionic acid, and cysteine hydrochloride;

(ii) a surfactant, comprising thiol and amine functional groups, selected from cysteine, mercaptoethylamine, thioguanine, and thioacetamide;

(iii) a surfactant, comprising thiol and hydroxyl groups, selected from mercaptoethanol, thiodiethanol, thioglucose, thioglycerol and cysteine-OH;

(iv) cysteine; or (v) a peptide consisting of a sequence of SEQ ID NO:1.

3. The nanoparticle complex of claim 1, wherein the surfactant(s) is: $HSCH_2COOH$, $HS(CH_2)_2COOH$ or a combination thereof.

4. The nanoparticle complex of claim 1, further comprising a biomolecule loaded on the surfactact(s).

5. The nanoparticle of claim 4, wherein the biomolecule is a drug.

6. The nanoparticle complex of claim 5, wherein the drug is selected from the group consisting of alkylating agents, antimetabolites, plant alkaloids, anti-tumour antibiotics, monoclonal or polyclonal antibody, a cytokine, an antisense oligonucleotide, siRNA, and a gene-targeting vector.

7. The nanoparticle complex of claim 6, wherein the drug is anti-cancer drug.

8. The nanoparticle complex of claim 5, wherein the drug is cisplatin, carboplatin, nedaplatin, satraplatin, methotraxate, doxorubicin or a combination thereof.

9. The nanoparticle complex of claim 4, wherein the surfactant is $HSCH_2COOH$, $HS(CH_2)_2COOH$ or a combination thereof, and the drug is cisplatin, carboplatin, nedaplatin, satraplatin, methotraxate, doxorubicin or a combination thereof.

10. The nanoparticle complex of claim 1, wherein the nanoparticle has a diameter of between 20 nm to 500 nm.

11. The nanoparticle complex of claim 1, wherein the nanoparticle is a nanocomposite of gold and sulphur.

12. The nanoparticle complex of claim 11, wherein the nanoparticle is a nanocomposite of $(Au_z)_{crystalline}$ $(Au_x—S_y)_{amorphous}$, wherein $3 \leq (z+x) \leq 30$ for $y=1$.

13. The nanoparticle complex of claim 11, wherein the nanoparticle is $Au—Au_2S$ nanoparticle.

14. A kit comprising:
NIR-sensitive nanoparticle(s); and
one or more surfactant(s);
wherein
the surfactant is at least one surfactant selected from:

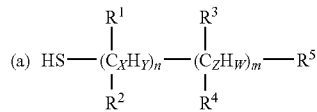

wherein X=1-9; Y=0-9; n=0-9; Z=1-9; W=0-9; m=0-9;

each of $R^1$, $R^2$, $R^3$ and $R^4$ independently, if present, is H, substituted or unsubstituted $C_1$-$C_6$ alkyl, substituted or unsubstituted $C_1$-$C_6$ aryl, HS, COOH, $NH_2$ or OH;

$R^5$ is COOH, $NH_2$ or OH;

with the proviso that n+m is <10;

(b) an amino acid having the structure in (a), wherein X=1; Y=2; Z=1; W=1; $R^1$, $R^2$ and $R^4$ are not present; $R^3$ is $NH_2$; and $R^5$ is COOH; or (c) a peptide, wherein the peptide comprise at least one amino acid (b) and consisting of a sequence of SEQ ID NO:1.

15. The kit claim 14, wherein the surfactant(s) is at least one or a mixture of the following:

(i) a surfactant, comprising thiol and carboxylic acid functional groups, selected from mercaptosuccinic acid, mercaptobenzoic acid, penicillamine, mercaptopropioinyl glycine, thioldiacetic acid, thiodipropionic acid, and cysteine hydrochloride;

(ii) a surfactant, comprising thiol and amine functional groups, selected from cysteine, mercaptoethylamine, thioguanine, and thioacetamide;

(iii) a surfactant, comprising thiol and hydroxyl groups, selected from mercaptoethanol, thiodiethanol, thioglucose, thioglycerol and cysteine-OH;

(iv) cysteine; or (v) a peptide consisting of a sequence of SEQ ID NO:1.

16. The kit of claim 14, wherein the surfactant(s) is: $HSCH_2COOH$, $HS(CH_2)_2OOH$ or a combination thereof.

17. The kit of claim 14, further comprising a biomolecule.

18. The kit of claim 17, wherein the biomolecule is a drug.

19. The kit of claim 18, wherein the drug is selected from the group consisting of alkylating agents, antimetabolites, plant alkaloids, anti-tumour antibiotics, monoclonal or polyclonal antibody, a cytokine, an antisense olignucleotide, siRNA, and a gene-targeting vector.

20. The kit of claim 18, wherein the drug is cisplatin, carboplatin, nedaplatin, satraplatin, methotraxate, doxorubicin or a combination thereof.

21. The kit of claim 14, wherein the nanoparticle is a nanocomposite of gold and sulphur.

* * * * *

UNITED STATES PATENT AND TRADEMARK OFFICE
CERTIFICATE OF CORRECTION

PATENT NO.       : 7,601,331 B2
APPLICATION NO.  : 10/985018
DATED            : October 13, 2009
INVENTOR(S)      : Chow et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1365 days.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,601,331 B2 |
| APPLICATION NO. | : 10/985018 |
| DATED | : October 13, 2009 |
| INVENTOR(S) | : Chow et al. |

It is certified that error appears in the above-identified patent and that said Letters Patent is hereby corrected as shown below:

On the title page, the Assignee information should be changed as follows:

Item (73) Assignee:   National University of Singapore,
                      Singapore (SG)

should be

(73) Assignee:   National University of Singapore,
                 Singapore (SG)

Massachusetts Institute of Technology
                 Cambridge (MA)

Signed and Sealed this

Ninth Day of November, 2010

David J. Kappos
*Director of the United States Patent and Trademark Office*